United States Patent
Scherer et al.

(10) Patent No.: US 12,144,620 B2
(45) Date of Patent: *Nov. 19, 2024

(54) SYSTEM AND METHODS FOR WIRELESS DRUG DELIVERY ON COMMAND

(71) Applicants: CALIFORNIA INSTITUTE OF TECHNOLOGY, Pasadena, CA (US); THE TRUSTEES OF DARTMOUTH COLLEGE, Hanover, NH (US)

(72) Inventors: Axel Scherer, Barnard, VT (US); Meisam Honarvar Nazari, Pasadena, CA (US); Muhammad Mujeeb-U-Rahman, San Gabriel, CA (US); Mehmet Sencan, Pasadena, CA (US); Arti Gaur, Hanover, NH (US)

(73) Assignees: CALIFORNIA INSTITUTE OF TECHNOLOGY, Pasadena, CA (US); THE TRUSTEES OF DARTMOUTH COLLEGE, Hanover, NH (US)

( * ) Notice: Subject to any disclaimer, the term of this patent is extended or adjusted under 35 U.S.C. 154(b) by 336 days.

This patent is subject to a terminal disclaimer.

(21) Appl. No.: 17/489,610

(22) Filed: Sep. 29, 2021

(65) Prior Publication Data

US 2022/0160264 A1 May 26, 2022

Related U.S. Application Data

(60) Continuation of application No. 16/437,890, filed on Jun. 11, 2019, now Pat. No. 11,160,476, which is a
(Continued)

(51) Int. Cl.
*A61B 5/1473* (2006.01)
*A61B 5/00* (2006.01)
(Continued)

(52) U.S. Cl.
CPC .......... *A61B 5/1473* (2013.01); *A61B 5/0031* (2013.01); *A61B 5/076* (2013.01);
(Continued)

(58) Field of Classification Search
CPC ...... A61M 2205/3523; A61M 2207/00; A61M 5/14276; A61M 2205/8237; A61M 5/172;
(Continued)

(56) References Cited

U.S. PATENT DOCUMENTS 5,797,898 A * 8/1998 Santini, Jr. ................ C25F 7/00
604/890.1
6,123,861 A * 9/2000 Santini, Jr. ........... A61K 9/0097
216/2
(Continued)

FOREIGN PATENT DOCUMENTS

| CN | 101398382 A | 4/2009 |
| CN | 102556952 A | 7/2012 |
| WO | 2009/133510 A1 | 11/2009 |

OTHER PUBLICATIONS

EP Patent Office Decision to Grant a European patent pursuant to Article 97(1) EPC ) in relation to EP Application No. 14829775.7 filed on Jul. 24, 2014 behalf of California Institute of Technology. Mail Date: Jun. 12, 2020. 1 Page.
(Continued)

*Primary Examiner* — Quynh-Nhu H. Vu
(74) *Attorney, Agent, or Firm* — Steinfl + Bruno LLP

(57) ABSTRACT

A fully integrated small size implantable sensing device is described, which can include a sensor and an electronic circuit to interface with the sensor and communicate with an external device. Various fabrication methods for the sensing device are described, including provision of wells, created using same fabrication technology as the electronic circuit, to contain electrodes of the sensor and corresponding func-
(Continued)

tionalization chemicals. Such implantable sensing device can be used for a variety of electrochemical measuring applications within a living body as well as actuation by injecting a current into the living body.

5 Claims, 32 Drawing Sheets

Related U.S. Application Data division of application No. 15/216,675, filed on Jul. 21, 2016, now Pat. No. 10,368,788.

(60) Provisional application No. 62/204,825, filed on Aug. 13, 2015, provisional application No. 62/195,895, filed on Jul. 23, 2015.

(51) Int. Cl.
| | |
|---|---|
| A61B 5/07 | (2006.01) |
| A61B 5/145 | (2006.01) |
| A61B 5/1459 | (2006.01) |
| A61B 5/1486 | (2006.01) |
| A61B 17/34 | (2006.01) |
| A61M 5/142 | (2006.01) |
| A61M 5/172 | (2006.01) |

(52) U.S. Cl.
CPC ........ *A61B 5/1451* (2013.01); *A61B 5/14532* (2013.01); *A61B 5/1459* (2013.01); *A61B 5/14865* (2013.01); *A61B 5/4839* (2013.01); *A61B 17/3468* (2013.01); *A61M 5/14276* (2013.01); *A61M 5/172* (2013.01); *A61M 5/1723* (2013.01); *A61B 5/14546* (2013.01); *A61B 5/14735* (2013.01); *A61B 2560/0219* (2013.01); *A61B 2562/0209* (2013.01); *A61B 2562/028* (2013.01); *A61B 2562/04* (2013.01); *A61B 2562/125* (2013.01); *A61M 2205/3523* (2013.01); *A61M 2205/8237* (2013.01); *A61M 2207/00* (2013.01)

(58) Field of Classification Search
CPC ........ A61B 17/3468; A61B 2560/0219; A61B 2562/028; A61B 2562/04; A61B 5/0031; A61B 5/076

See application file for complete search history.

(56) References Cited

U.S. PATENT DOCUMENTS

| | | | |
|---|---|---|---|
| 6,201,980 B1 | 3/2001 | Darrow et al. | |
| 6,968,743 B2 | 11/2005 | Rich et al. | |
| 7,031,768 B2* | 4/2006 | Anderson | A61N 1/0436 604/20 |
| 7,548,778 B2* | 6/2009 | Roy | A61F 9/0017 604/20 |
| 7,894,870 B1 | 2/2011 | Lucisano et al. | |
| 8,231,609 B2 | 7/2012 | Pang et al. | |
| 8,332,028 B2* | 12/2012 | Visco | A61N 1/044 424/722 |
| 9,789,315 B2* | 10/2017 | Dacey, Jr. | A61N 1/327 |
| 10,368,788 B2* | 8/2019 | Scherer | A61B 5/1459 |
| 11,160,476 B2 | 11/2021 | Scherer et al. | |
| 11,510,573 B2 | 11/2022 | Mujeeb-U-Rahman et al. | |
| 2001/0039374 A1 | 11/2001 | Schulman | |
| 2002/0072784 A1* | 6/2002 | Sheppard, Jr. | A61K 9/0009 607/60 |
| 2005/0055014 A1* | 3/2005 | Coppeta | A61K 9/0009 604/890.1 |
| 2005/0143715 A1* | 6/2005 | Cima | A61K 9/0009 604/890.1 |
| 2006/0076236 A1 | 4/2006 | Shah et al. | |
| 2006/0079740 A1 | 4/2006 | Silver et al. | |
| 2006/0270923 A1 | 11/2006 | Brauker et al. | |
| 2008/0188725 A1 | 8/2008 | Markle et al. | |
| 2008/0302659 A1* | 12/2008 | Sheppard, Jr. | C12Q 1/004 204/403.01 |
| 2013/0030271 A1 | 1/2013 | Lang et al. | |
| 2013/0313130 A1 | 11/2013 | Little et al. | |
| 2013/0338773 A1 | 12/2013 | Boyden et al. | |
| 2014/0107446 A1 | 4/2014 | Tolosa et al. | |
| 2015/0133339 A1 | 5/2015 | Prindle et al. | |
| 2015/0265182 A1 | 9/2015 | Jain et al. | |
| 2019/0290171 A1 | 9/2019 | Scherer et al. | |
| 2021/0093233 A1 | 4/2021 | Scherer et al. | |
| 2023/0233082 A1 | 7/2023 | Mujeeb-U-Rahman et al. | |

OTHER PUBLICATIONS

Non-Final Office Action for U.S. Appl. No. 17/037,207, filed Sep. 29, 2020 on behalf of California Institute of Technology et al. Mailed on Dec. 26, 2023. 21 pages.

Notice of Allowance for U.S. Appl. No. 16/457,642, filed Jun. 28, 2019 on behalf of California Institute of Technology Mail Date: Aug. 22, 2022 8 pages.

Non-Final Office Action issued for U.S. Appl. No. 16/457,642, filed Jun. 28, 2019, on behalf of California Institute of Technology. Mail Date: May 13, 2022. 12 Pages.

Final Office Action for U.S. Appl. No. 17/037,207, filed Sep. 29, 2020 on behalf of California Institute of Technology et al. Mailed on May 29, 2024. 30 pages.

First Office Action for Chinese Application No. 201380072813.5 filed on Dec. 12, 2013 on behalf of California Institute of Technology. Mailed on Dec. 28, 2016. 16 pages. Original and English translation.

\* cited by examiner

|  | This work | [1] | [2] |
|---|---|---|---|
| Carrier frequency | 900 MHz | 13.56 MHz | 1.8GHz |
| Power consumption | 6μW | 110μW | 3μW |
| System size | 1.4mm×1.4mm | 8mm×4mm | 1cm diameter* |
| External Component | No | Yes | Yes |
| Read range | 1cm (5mm tissue) | 4cm (in Air) | 15cm (in Air, EIRP 40dBm) |
| Glucose detect range | 0-20mM (tissue fluid) | 0-40mM (Blood) | 0-2mM (tear) |

* Including off-chip antenna size.

FIG. 22

SYSTEM AND METHODS FOR WIRELESS DRUG DELIVERY ON COMMAND

CROSS REFERENCE TO RELATED APPLICATIONS

The present application is a Continuation of U.S. patent application Ser. No. 16/437,890 filed on Jun. 11, 2019, which, in turn, is a Divisional of U.S. Pat. No. 10,368,788 issued on Aug. 6, 2019, which, in turn, claims priority to U.S. Provisional Application No. 62/195,895 filed on Jul. 23, 2015, and U.S. Provisional Application No. 62/204,825 filed on Aug. 13, 2015, the disclosures of all of which are incorporated herein by reference in their entirety.

The present application is related to U.S. application Ser. No. 15/216,662 entitled "Canary on a Chip: Embedded Sensors with Bio-Chemical Interfaces" filed on Jul. 21, 2016, the disclosure of which is incorporated herein by reference in its entirety.

The present application may be related to U.S. Pat. No. 9,006,014 entitled "Fabrication of Three-Dimensional High Surface Area Electrodes", issued Apr. 14, 2015, the disclosure of which is incorporated herein by reference in its entirety.

The present application may be related to US Patent Publication No. 2014/0228660 entitled "Miniaturized Implantable Electrochemical Sensor Devices", published Aug. 14, 2014, the disclosure of which is incorporated herein by reference in its entirety.

The present application may be related to U.S. Pat. No. 9,177,933 entitled "Three-Dimensional High Surface Area Electrodes", issued Nov. 3, 2015, the disclosure of which is incorporated herein by reference in its entirety.

The present application may be related to U.S. Pat. No. 9,173,605 entitled "Fabrication of Implantable Fully Integrated Electrochemical Sensors", issued Nov. 3, 2015, the disclosure of which is incorporated herein by reference in its entirety.

STATEMENT OF GOVERNMENT GRANT

This invention was made with government support under Grant No. EB020416 awarded by the National Institutes of Health. The government has certain rights in the invention.

TECHNICAL FIELD

The present disclosure relates to design, fabrication and usage of implantable fully integrated devices which can be used as electrochemical sensor devices and/or as drug delivery devices in-vivo.

BACKGROUND

The measurement of biological indicators is of interest for a variety of medical disorders. Various systems have been developed to measure biological indicators from within the living body (in-vivo) of various animals (e.g. mammals) via an implantable device. It is now possible to build compact devices that can measure metabolites and perform electrophysiology with wireless interfaces that communicate with external controllers/data readers. It would be desirable to use such technologies to deliver biochemical molecules with precise control over their quantity, location and time.

Existing implantable devices have the potential to create high local temperatures inside the living body. Often power provided from external sources results in an increase in local temperature around the implantable device. Often transmission of information from the implantable device results in an increase in local temperature around the implantable device. The living body, however, cannot tolerate high internal temperatures. High internal temperatures often lead to tissue death [e.g. reference 5, herein incorporated by reference in its entirety].

Another issue facing implantable devices is the formation of a foreign body capsule in the tissue of the living body around the implantable device. Fibrogen and other proteins bind to the device surface shortly after implantation in a process known as biofouling. Macrophages bind to the receptors on these proteins releasing growth factor β and other inflammatory cytokines. Procollagen is synthesized and becomes crosslinked after secretion into the extracellular space gradually contributing to formation of a dense fibrous foreign body capsule. The dense capsule prevents the implantable device from interfacing with the living body and thereby often hinders the operation of the implantable device [e.g. reference 6, herein incorporated by reference in its entirety].

These issues have been addressed to some extent by a miniaturized implantable electrochemical sensor device disclosed in afore mentioned related U.S. Patent Publication No. 2014/0228660, incorporated herein by reference in its entirety. However, such miniaturized implantable electrochemical sensor is not fully integrated (e.g. monolithically integrated) as some of its elements are glued onto the device.

In particular, fully wireless implants are being considered as the future of health care system. These implants can improve the health care system in many aspects. The ultra-small scale design of these devices promises many advantages compared to their macro counterparts. This size scale is perceived to minimize the foreign body response to an implant. It would also enable easy implantation and explantation procedures. Finally, such implants can minimize the permanent risk of infection and irritation associated with wired systems currently being used, such as transcutaneous continuous glucose monitoring (CGM) systems. In many situations, CGM system being a relevant example, a remotely powered implanted sensor can monitor levels of signals of interest and transmit data to an external receiver/controller avoiding risks associated with such wired implants. To allow for reliable power delivery as well as minimizing foreign body response, both the sensor's size and power dissipation can be minimized. To date, implantable devices that can be used as miniaturized drug delivery devices have not been reported. It follows that the present disclosure provides methods and devices which can be used to fabricate miniature size implantable devices for applications related to controlled delivery of biochemical molecules which in some cases can also be coupled with measurement of body fluids, not limited to measurement in a specific environment, and which can be used for a broad range of applications, such as the described "Canary on a Chip" application.

SUMMARY

Solid State electrochemical sensors and actuators at Micro/Nano scale have gained lots of interest in recent years. Detailed design of such sensors and actuators using micro/nano technologies can involve many system level design issues which need to be addressed together to get an optimal response for a particular application. In some cases, special design/fabrication/manufacturing techniques can be used so as to allow these devices to be part of a completely integrated system. The present application discloses such techniques for exemplary cases of implantable integrated systems, which cases should not be construed as limiting the scope of the present teachings. It is understood that a person skilled in the art can use these same techniques for design/fabrication/manufacturing of other types of integrated solid state electrochemical sensors and actuators using micro and/or nano technologies. Such implantable integrated systems can allow minimally invasive micro-sensors to monitor, in-vivo, response of cells to specific analytes, and further allow triggering of therapeutic agents stored in microchambers via integrated actuators.

According to one embodiment the present disclosure, a method for fabricating a miniaturized implantable device is presented, the method comprising: fabricating an electronic system by monolithically integrating the electronic system on a first face of a substrate, the electronic system comprising an energy storage element adapted to be charged through a wireless communication link; fabricating a coil by monolithically integrating the coil on the first face of the substrate, the coil being configured to provide the wireless communication link; and fixating at least one hermetic package, containing a liquid payload, on the first surface of the substrate, a portion of the hermetic package being positioned above the coil, wherein the energy storage element is configured to provide energy to rupture a seal of the hermetic package, thereby dispensing the liquid payload.

According to a second embodiment of the present disclosure, an integrated miniaturized implantable device is presented, comprising: a substrate for monolithic integration comprising a plurality of metal layers separated via a plurality of insulating layers; a monolithically integrated electronic system comprising an energy storage element adapted to be charged through a wireless communication; a monolithically integrated coil configured to provide the wireless communication link; and a hermetic package, containing a liquid payload, fixated on the substrate, a portion of the hermetic package being positioned above the coil, wherein during operation of the implantable device, the electronic system is configured to: communicate with an external device over the wireless communication link provided by the coil, extract power for the miniaturized implantable device from the wireless communication link, charge the energy storage element based on the extracted power, and energize an actuator via the energy storage element to rupture a seal of the hermetic package.

Further aspects of the disclosure are shown in the specification, drawings and claims of the present application.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIG. 22 shows a table representative of various performances of the exemplary implementation.

DETAILED DESCRIPTION

Figure 1A:
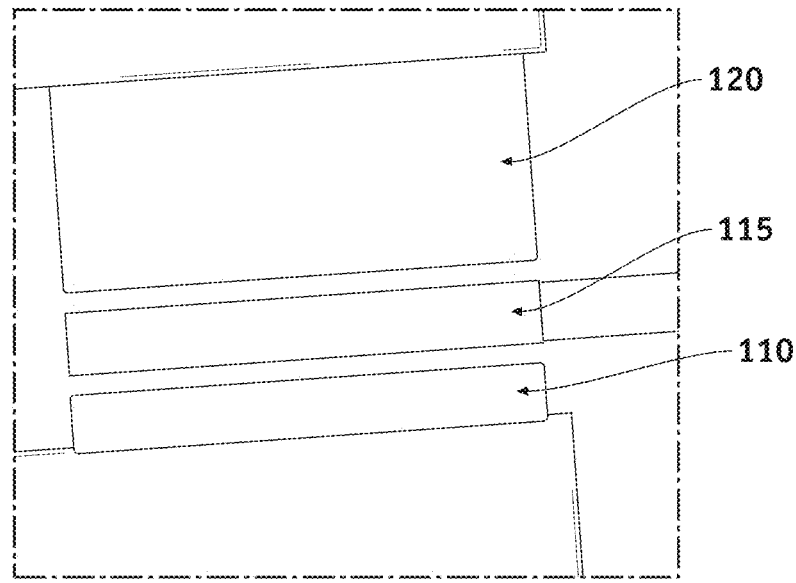
FIGS. 1A and 1B illustrate exemplary geometries of electrodes used for a sensor of an integrated implantable device according to embodiments of the present disclosure.

As used herein, a "monolithic substrate" is a substrate upon which components are monolithically integrated and therefore such components are not adhered and/or secured via mechanical means to the substrate. In various embodiments according to the present disclosure the monolithic substrate can be the result of processing using CMOS technology or other fabrication technology known to the skilled person. It is understood that a monolithic substrate has multiple faces, and at least a first face and a second face. A first and second face can be distinguished from other faces of the monolithic substrate in that the first and second face are larger than the other faces of the monolithic substrate.

As used herein, the term "sensor" can refer to the region of the implantable device responsible for the detection of a particular biological indicator. For example, in some embodiments for glucose monitoring, the sensor interface refers to that region wherein a biological sample (e.g., blood or interstitial fluid) or portions thereof contacts an enzyme (e.g. glucose oxidase); a reaction of the biological sample (or portion thereof) results in the formation of reaction products that allow a determination of the glucose level in the biological sample. In various embodiments of the present invention, the sensor further comprises a "functionalization layer" as described later in the present disclosure. In various embodiments of present disclosure the sensor can be monolithically integrated into the monolithic substrate. In various embodiments of the present disclosure the monolithically integrated sensor can be placed on a different face of the monolithic substrate from a corresponding signal processing circuit. This can be done in various embodiments by forming for example high surface electrodes (e.g. patterned electrodes) similarly to the method described below on a silicon face of the monolithic substrate and interconnecting them through the monolithic substrate to the other face of the monolithic substrate comprising the signal processing circuit. More information on sensors and patterned electrodes and construction methods thereof can be found, for example, in the referenced U.S. Pat. No. 9,006,014 entitled "Fabrication of Three-Dimensional High Surface Area Electrodes", issued Apr. 14, 2015, herein incorporated by reference in its entirety.

Fully integrated electrochemical sensor devices can be attractive in a variety of applications requiring measurement of different species in different environments. For the case of implantable sensing applications, these devices can detect/provide very selective and sensitive signal as well as ease of integration with signal processing platforms using, for example, CMOS technology.

According to the various embodiments of the present disclosure presented in the following sections, full integration of these devices can be achieved by using design methods that takes into account the presence of the complete system around the electrochemical sensors. Furthermore, fabrication methods and techniques according to the various embodiments of the present disclosure used for the integrated devices are compatible with the complete system and do not affect the performance of any corresponding subsystem substantially.

An electrochemical sensor (e.g. a potentiometric/amperometric sensor) can consist of multiple electrodes. Commonly three electrodes are used, a working electrode, a counter electrode and a reference electrode. The reference electrode can be used to establish a stable potential reference in a target measurement environment (e.g. a chemical solution, blood, interstitial fluid, etc.)). The working electrode can be used for generating an electrical signal (e.g. a current flow) corresponding to some interface reaction of one or more specie of interest within the target measurement environment. The counter electrode, which can be a passive element of a circuit comprising the electrochemical sensor in the target measurement environment, can generally be used to balance the current of the working electrode. For some systems where very small signals are generated, the reference electrode can also act as the counter electrode and therefore eliminating the need for a third electrode. For some other systems where placement of a reference electrode can be difficult, a floating reference-less (electrode) design can be used. A four or more electrode design can also be used where more than one working electrodes can be used to measure differential signal levels for better noise immunity or multiple species at a time.

For implantable sensor applications (e.g. humans, mammals) where size of the sensor is of importance, the floating reference-less design can result in smaller device footprint. However, if long term stability of an implantable sensor is a major design issue, three electrode design with a dedicated and stable reference electrode can be a more attractive design approach.

Micro/Nano scale structuring of integrated electrodes can provide many useful features for a variety of applications. Methods for designing and fabricating such integrated electrodes are disclosed by Applicants of the present disclosure in the above referenced U.S. Pat. No. 9,006,014 entitled "Fabrication of Three-Dimensional High Surface Area Electrodes", issued Apr. 14, 2015, herein incorporated by reference in its entirety.

For implantable sensor applications where selectivity of the sensor is desirable, functionalization of the corresponding electrodes can be a useful technique. Sensors according to the various embodiments of the present disclosure are designed to easily incorporate in situ functionalization (e.g. electrodes can be functionalized after fabrication/integration within the integrated sensor device). The micro/nano scale geometry of the sensors coupled with a well structure around the sensors, as described in the above referenced U.S. Pat.

No. 9,006,014, issued Apr. 14, 2015, and US Patent Publication No. 2014/0228660, published Aug. 14, 2014, which are both incorporated herein by reference in their entirety, make such functionalization possible by retaining the functionalization matrix in its place.

As known to a person skilled in the art, functionalization is a process by which the electrodes of the sensor are covered by a "functional layer" to provide specificity to a target of interest. The phrase "functional layer" refers to a layer comprising any mechanism (e.g., enzymatic or non-enzymatic) by which a target of interest can be detected into an electronic signal for the device. For example, according to some embodiments of the present invention, a functional layer can contain a gel of glucose oxidase that catalyzes the conversion of glucose to gluconate: Glucose+$O_2 \rightarrow$Gluconate+$H_2O_2$. Because for each glucose molecule converted to gluconate, there is a proportional change in the co-reactant $O_2$ and the product $H_2O_2$, one can monitor the current change in either the co-reactant or the product to determine glucose concentration. In various embodiments of the present disclosure the functional layer can comprise a hydrogel (e.g. BSA) loaded with an enzyme (e.g. glucose oxidase). In various alternative embodiments of the present disclosure the functional layer can also be a polymer (e.g. polypyridine) loaded with an enzyme (e.g. glucose oxidase).

According to the various embodiments of the present disclosure, method for design, fabrication and manufacturing of solid state electrochemical systems on very small (Micro/Nano) scale on integrated platform are presented next. Such solid state electrochemical systems can incorporate sensors using micro and nano scale features, and corresponding signal processing circuits designed using, for example, CMOS technology, all integrated within a millimeter size implantable device. In an exemplary embodiment according to the present disclosure, such implantable device can have a surface area no larger than 1.4 mm×1.4 mm and down to 1.0 mm×1.0 mm, and a thickness no larger than 250 μm with no functionalization layer chemistry applied, and no larger than 0.5 mm including the functionalization layer and a protective layer. Furthermore, the die (e.g. CMOS die used for fabrication) can be further thinned down (e.g. from a back side of the die) to about 100 μm (e.g. from 250 μm) to provide an even thinner device, of thickness no larger than 200 μm and down to about 100 μm with no functionalization layer chemistry applied. In some embodiments functionalization layer chemistry can have a thickness of about or smaller than 200 μm and the protective layer (e.g. packaging, biocompatibility/diffusion limiting gel) can have a thickness of about or smaller than 100 μm. Accordingly, the integrated implantable device, in its finished state, can have a total size of about 1.0 mm×1.0 mm×200 μm to 1.0 mm×1.0 mm×400 μm, depending on requirement or not of the protective layer and thickness of the functionalization layer (e.g. whether or not the functionalization layer can be fully embedded within the later described wells).

Sensor Design

Three electrode based designs, as described in previous sections of the present disclosure and known to the person skilled in the art, can be the common choice for stable performance in long term applications (e.g. expected continuous usage of possibly several months). According to an embodiment of the present disclosure an optional fourth electrode can be used to perform background noise cancellation and/or differential calibration. Since design constraints of the implantable integrated device can include total available area, according to some embodiments of the present disclosure the fourth electrode can be used if a decrease in size of the other electrodes such as to compensate for placement of the fourth electrode (and corresponding additional signal processing components) does not compromise their performance. Inclusion of additional signal processing for a fourth electrode can also increase size and power consumption of on-chip signal processing circuitry. This can also be taken into account during the design of the implantable integrated device. Although exemplary cases of three and four electrode sensor designs are mentioned in this section of the present disclosure, the skilled person readily knows that these are mere exemplary in nature as alternative designs using, for example, 2 and more than 4 electrodes sensors are also possible given the present teachings.

When the electrochemical sensor is within a target measuring environment to detect a specie of interest, some current can exist which is caused by sources other than the specie of interest. Such current, which can be referred to as background current, can be caused by circuit noise, interfering chemicals (e.g. acetaminophen, L-ascorbic acid, etc. in the case of $H_2O_2$ based sensors), as well as detected species not produced by a sensing chemistry of the electrochemical sensor (e.g. background levels of $H_2O_2$ or $O_2$). For applications where the background signal of the target measurement environment changes rapidly, the use of a fourth electrode can be beneficial to reduce the effects of such rapid changes on a detected signal. In the case of implantable applications, severity of such effects can depend on whether or not the electrode chemistry can minimize the background changes, such as for example, by blocking out interfering chemicals such as acetaminophen and L-ascorbic acid. If the electrode chemistry can minimize the background changes, then three electrodes can be sufficient, and if not, a fourth electrode which can be used for differential measurement can be beneficial.

Once the total area and number of electrodes is established (e.g. as presented in the previous sections of the present disclosure), according to further embodiments of the present disclosure the working electrode surface area of the electrodes can be established according to a desired signal-to-noise ratio from the background signal. This can be established via a combination of mathematical modeling, computer simulations and experimental results. Once the working electrode surface area is established, the counter electrode is designed to have a surface area multiple times larger (e.g. 3-20 times larger) than the working electrode so as to avoid any loading of the sensor signal. The reference electrode can be designed to have a surface area comparable to the working electrode in size, to put it at close proximity to most of the working electrode so as to minimize iR drop between the two electrodes (e.g. due to the uncompensated resistance between the two electrodes). Finally, the reference electrode can be placed closest to the working electrode rather than to counter electrode.

Figure 1B:
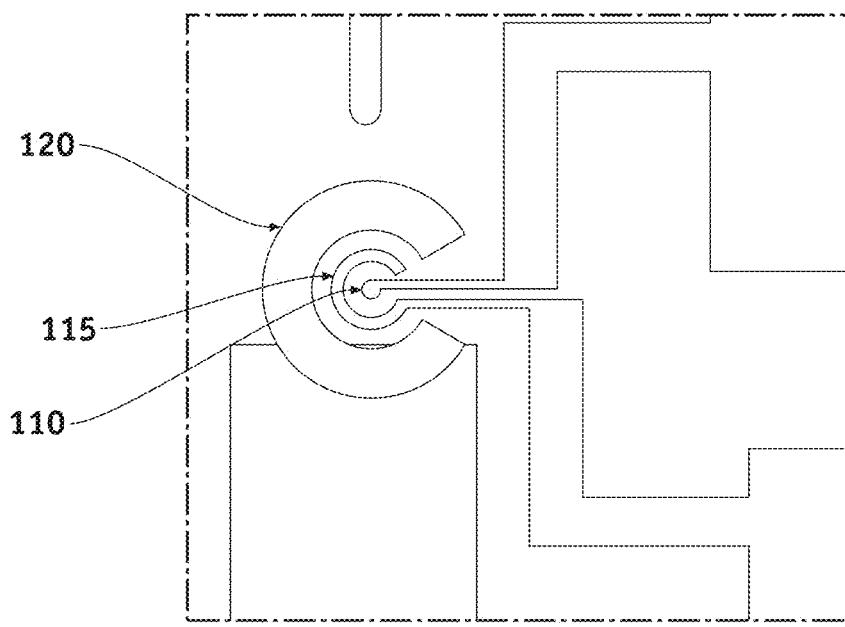

According to further embodiments of the present disclosure, said constraints related to number of electrodes and total available surface area for the electrodes can be fulfilled by different geometries of the electrodes. A geometrical approach can be used to optimize the design iteratively. Two exemplary design geometries of sensors and associated electrodes are shown in FIGS. 1A and 1B. Both sensors depicted in FIGS. 1A and 1B can cover a same surface and can have three electrodes, such as, for example, a working electrode (WE), a reference electrode (RE), and a counter electrode (CE) respectively identified as (110, 115, 120) in FIGS. 1A and 1B.

Figure 2:
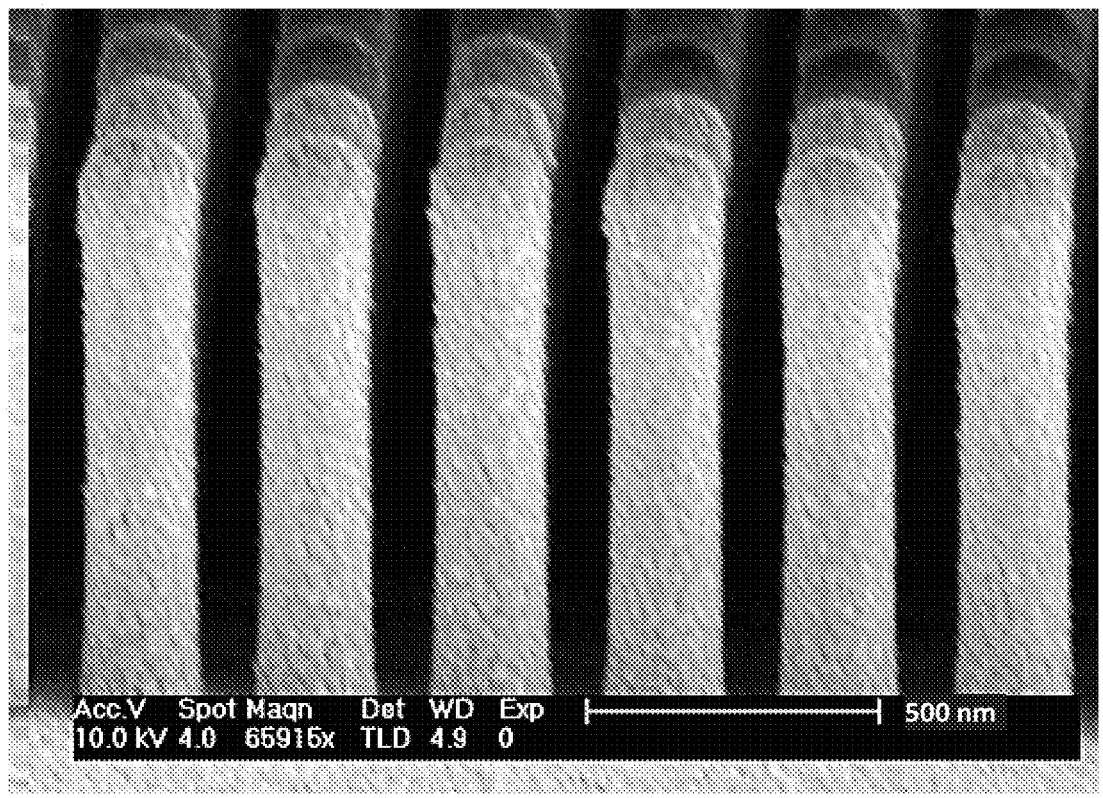
FIG. 2 illustrates an exemplary embodiment of a patterned electrode surface.

The sensors shown in FIGS. 1A and 1B can have planar electrodes. According to some embodiments and depending upon specific applications and requirements, one or more of the electrodes of the sensors can be patterned. Patterned electrodes can be utilized to enhance performance as they can possess an increased effective surface area relative to planar (e.g. non-patterned) electrodes, as described, for example, in the referenced U.S. Pat. No. 9,006,014 entitled "Fabrication of Three-Dimensional High Surface Area Electrodes", issued Apr. 14, 2015, herein incorporated by reference in its entirety. An example of a patterned electrode is shown in FIG. 2.

In exemplary embodiments according to the present disclosure the design of the patterned electrodes can be made using commercial software. PMMA 950 A4 can be used to achieve clean lift-off while still achieving a desired resolution. The resist can be spun at 4000 rpm for 1 minute followed by a 180° C. bake for 5 minutes. A dose of 1200 μc/cm2 can be used to write the pattern in a Leica EBPG5000+ optical system. Patterns can be developed in 1:3 solution of MIBK and IPA for 20 seconds followed by a deionized water rinse. Afterwards, a 50 nm alumina mask can be sputter coated in a Temescal TES BJD-1800 DC reactive sputter system by depositing aluminum in oxygen plasma for 5 minutes. Lastly, mask liftoff can be performed in dicholoromethane in an ultrasonic bath for 2 minutes. Successful patterning was confirmed by the applicants of present disclosure via optical microscopy (not shown).

In exemplary embodiments according to the present disclosure patterning can next be performed with a MA-N 2403 resist. Pillars can be fabricated using both dry plasma (C12:BC13) as well as wet etchants (e.g. TMAH) to etch away parts of the metal pad using, for example, a UNAXIS RIE machine. For the dry plasma (C12:BC13) etch, the temperature can be set to 25 degrees Celsius and RIE power to 120 watts. Flow rate for C12 can be set to 4 SCCM and the flow rate of BC13 can be set to 20 SCCM. For the wet TMAH etch, the surface can be submerged in a liquid at room temperature for 10 minutes. Success can be seen in the dimensions and uniformity of the formed structure.

According to a further embodiment of the present disclosure, such sensors, either planar or patterned (e.g. comprising planar/patterned electrodes), can also be fabricated on the front side of the IC substrate. In an exemplary embodiment according to the present disclosure construction methods for metal structures available in CMOS technology can be used to fabricate such planar and/or patterned sensors. These can be combined (e.g. integrated) with the construction steps related to the electronic IC, including connections between the sensor and the IC. In yet another exemplary embodiment according to the present disclosure, an exposed silicon area on the front surface can be used to fabricate such planar and/or patterned sensors during a post-processing step (e.g. after the CMOS processing step). According to yet another exemplary embodiment according to the present disclosure, planar and/or patterned sensors can be fabricated on a top metal layer using same fabrication technology (e.g. CMOS) as the required electronics, while the required electronics (e.g. IC) can be designed under the top metal layer (e.g. either fully or partially) to reduce the overall die area. In the case of the latter exemplary embodiment, spacing between the electrodes can be utilized to allow, for example, optical/RF waves, to reach optical/RF elements (e.g. integrated photovoltaic devices, RF antennae) which can be placed on a lower level below a level corresponding to the top metal layer. Such waves can be used to transmit/receive signals from/to the integrated device's electronic circuit. The person skilled in the art will know how to use such teachings according to the present disclosure for transmission/reception of other types of signals through regions of the top metal layer.

Figure 3A:
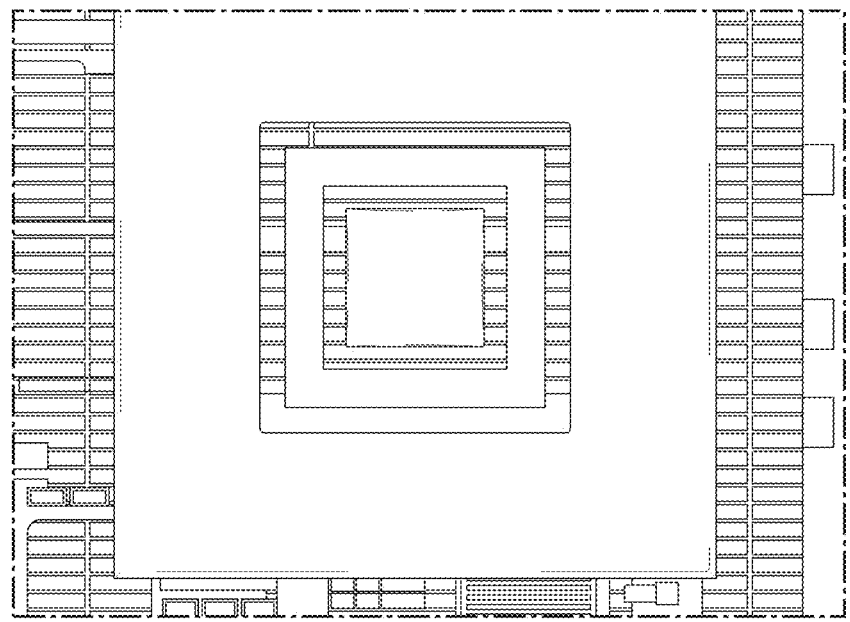
FIGS. 3A and 3B illustrate exemplary geometries of sensors used for the integrated implantable device according to embodiments of the present disclosure.
Figure 3B:
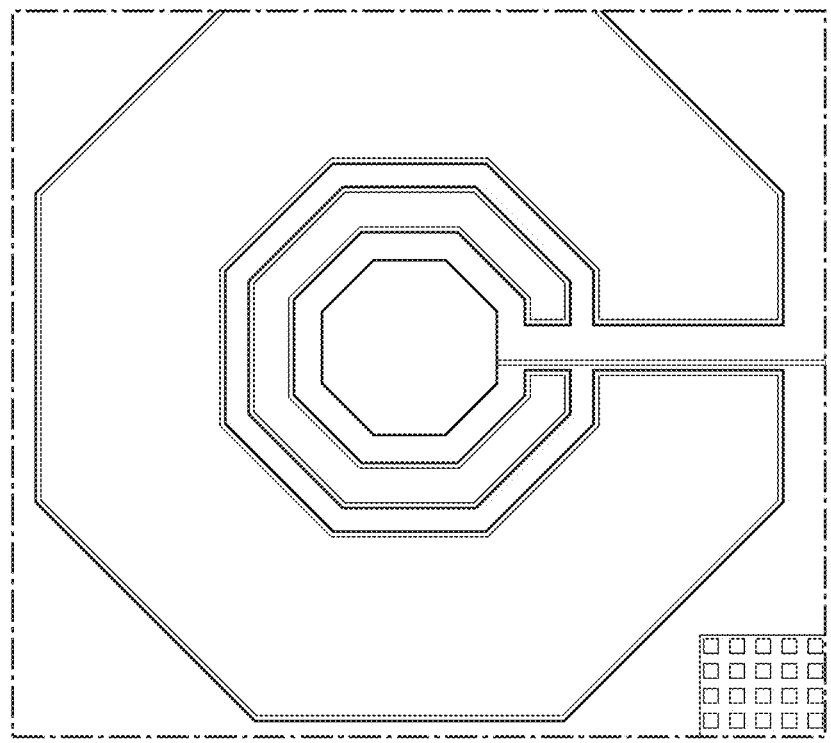

With further reference to a combined method of fabricating the sensors and the underlying electronics, according to some embodiments of the present disclosure, sensor design can be integrated within the design of the underlying electronic circuitry, using, for example, CMOS fabrication technology. Using such fabrication technology, exemplary sensor (e.g. two, three or higher electrodes) geometries can include rectangular as well as polygonal integrated sensors on a corresponding CMOS chip, as depicted in FIG. 3A (rectangular sensor) and FIG. 3B (polygonal sensor). According to some exemplary embodiments of the present disclosure, such integrated sensors can be fabricated during a CMOS processing phase using a top metal layer in a stack of metal layers (e.g. of a CMOS substrate) used in the CMOS fabrication. As known to a person skilled in the art, CMOS fabrication process can use a plurality of metal layers for interconnection. Such layers can be stacked on top of each other with insulator layers (e.g. oxide layers) separating them. Top metal layer as used herein is referred to the top most metal layer in the stack of metal layers, which generally can have a top insulator layer (e.g. top most insulator layer) above it. Therefore, a lower metal layer can be a metal layer of the stack below the top metal layer. In alternative embodiments according to the present disclosure, the integrated sensors can be fabricated during a CMOS processing phase using a lower metal which can be later exposed using further etching of top insulating layers (e.g. oxide layers which can separate a top metal layer from the lower metal layer). Latter method using a lower metal can provide a deeper well (e.g. for depositing a different metal and/or functionalization chemistry, later described) for corresponding sensors electrodes and therefore can allow for increasing the thickness of functionalization chemistry on top of the electrodes, although according to some embodiments of the present disclosure such well may comprise portion of and not all the functionalization layer.

In some cases common metals available in the processing phase of the underlying electronics (e.g. CMOS) are not very suitable for electrochemical sensing applications. For example, CMOS processing typically can use Al, Cu, Al/Cu metal alloys which can be undesirable for electrochemical sensing applications. It follows that according to further embodiments of the present disclosure such undesirable metals can be covered (e.g. using electron beam deposition) or replaced (e.g. using etching followed by deposition) with more suitable metals for electrochemical sensing during a corresponding post-processing step. These more suitable metals can be, for example, noble metals (e.g. platinum-based (Pt) metals, Iridium-based (Ir) metals, gold-based (Au) metals). More information about this post-processing step is provided in later sections of the present disclosure.

Integration of the electrodes into the chip (e.g. fabricated via CMOS process) used for the electronics of the sensor device and the corresponding post-processing method as per the described embodiments of the present disclosure can provide advantages which the person skilled in the art can appreciate. For example, such integrated sensor design can avoid the need to bond separate sensor dies to the electronic chip (e.g. CMOS) which in can therefore reduce a corresponding system size and eliminate noise due to extra wiring required between the electronic chip and a non-integrated sensor. Such integrated electrodes can be fabricated on a same side (e.g. referred to as top side) of the die as the underlying electronic circuitry is fabricated (e.g. via CMOS process).

Figure 4A:
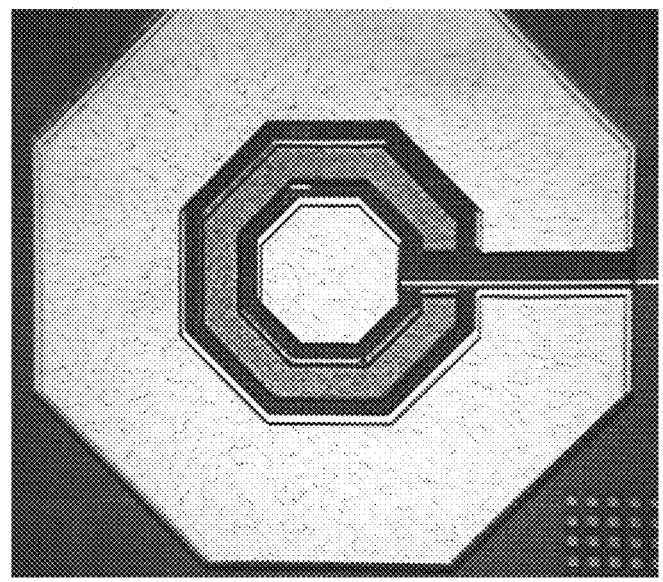
FIGS. 4A and 4B illustrate two sensors whose electrodes are covered using two different deposition methods.
Figure 4B:
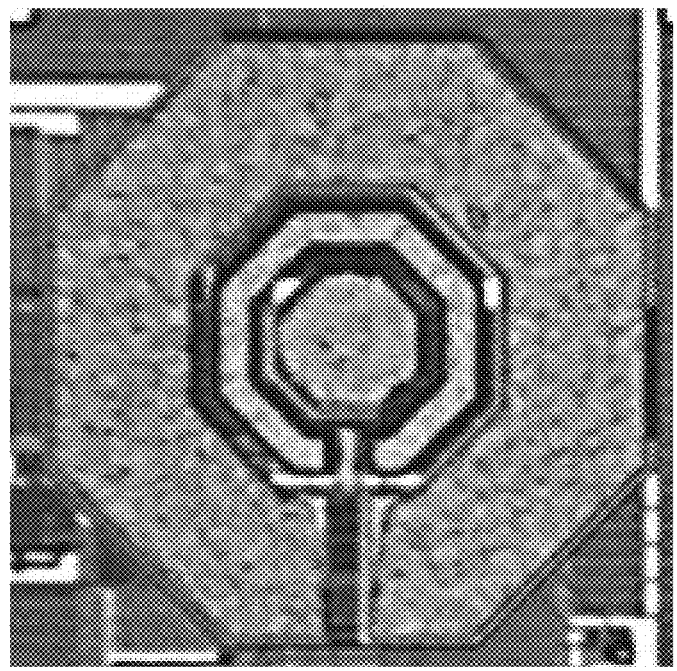

With further reference to the post-processing step for fabrication of the integrated sensors, corresponding desirable metal deposition methods can include electron beam deposition for planar coatings or sputtering for more conformal coatings of patterned electrodes. Other methods known to the skilled person, such as thermal evaporation, can also be used during this post-processing step. FIGS. 4A and 4B depict integrated CMOS sensors (e.g. electrodes) where corresponding electrodes are covered with desirable metals using two different deposition methods; FIG. 4A depicts an integrated CMOS sensor deposited via electron beam deposition method and FIG. 4B depicts an integrated CMOS sensor deposited via sputtering method.

In exemplary embodiments according to the present disclosure, metal deposition can be performed by sputtering which can also provide conformal coatings. First high density Argon plasma of 20 mTorr can be used to increase the isotropy of the deposition. A 5 nm Ti adhesion layer can be DC sputtered and then 50 nm or 100 nm Au or Pt films can be DC sputtered. A special stage can be used which can tilt the sample with respect to the incoming metal atoms at angles up to 90° C. Secondly, the stage can rotate at speeds up to 120 r.p.m. A combination of tilt and rotation along with optimization of plasma parameters (high pressure, around 20 mTorr) resulted in very uniformly controlled conformal sidewalls, as witnessed by the applicants of the present disclosure.

Figure 5:
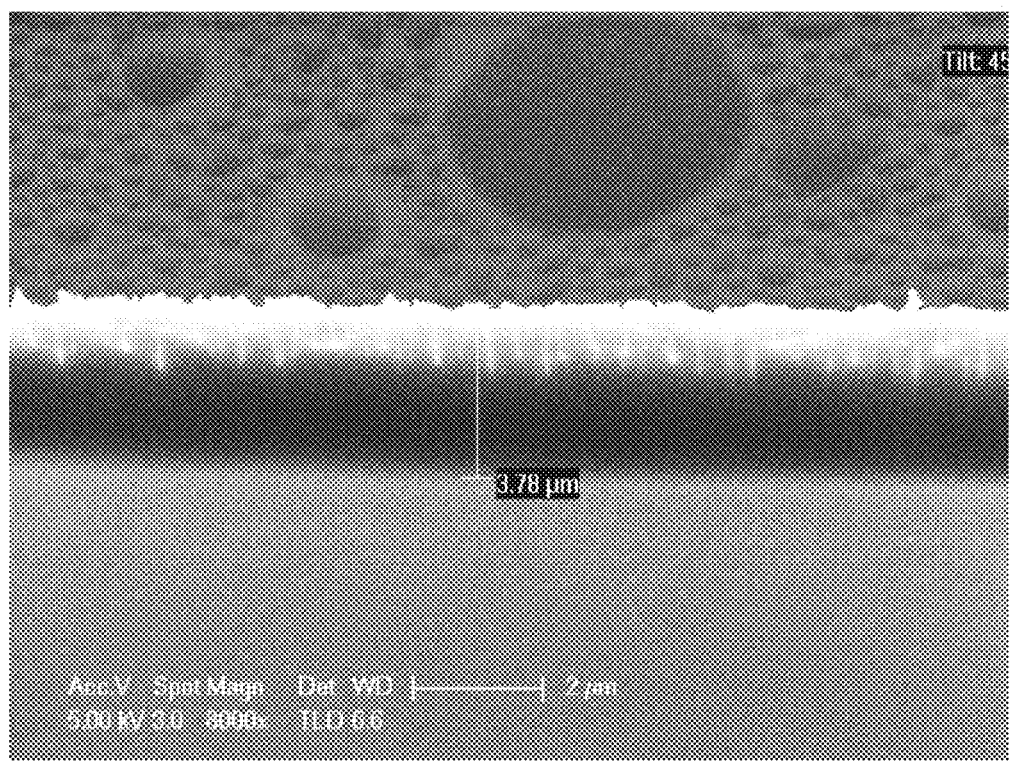
FIG. 5 shows a well of the integrated implantable device created using a CMOS process which can be used to hold an electrode and/or functionalization chemistry.

According to further embodiments of the present disclosure, electrode metals created via the chip manufacturing process, such as CMOS, can be etched (e.g. completely) so as to create wells that can be used to deposit more suitable metals and to provide for thicker electrodes if desirable. In combination, such wells can also be used to hold all or portion of the functionalization chemistry. One such well created by etching a top metal is shown in FIG. 5, which depicts an angled view of a sidewall of the well, which in the exemplary case of FIG. 5, has a measured depth of 3.78 µm. Exemplary well thickness can be about 4 µm although thicker wells in the range of 5 µm-6 µm can be obtained by etching lower layers of the substrate. It should be noted that the various embodiments according to the present disclosure can be provided either with or without the wells.

Figure 6:
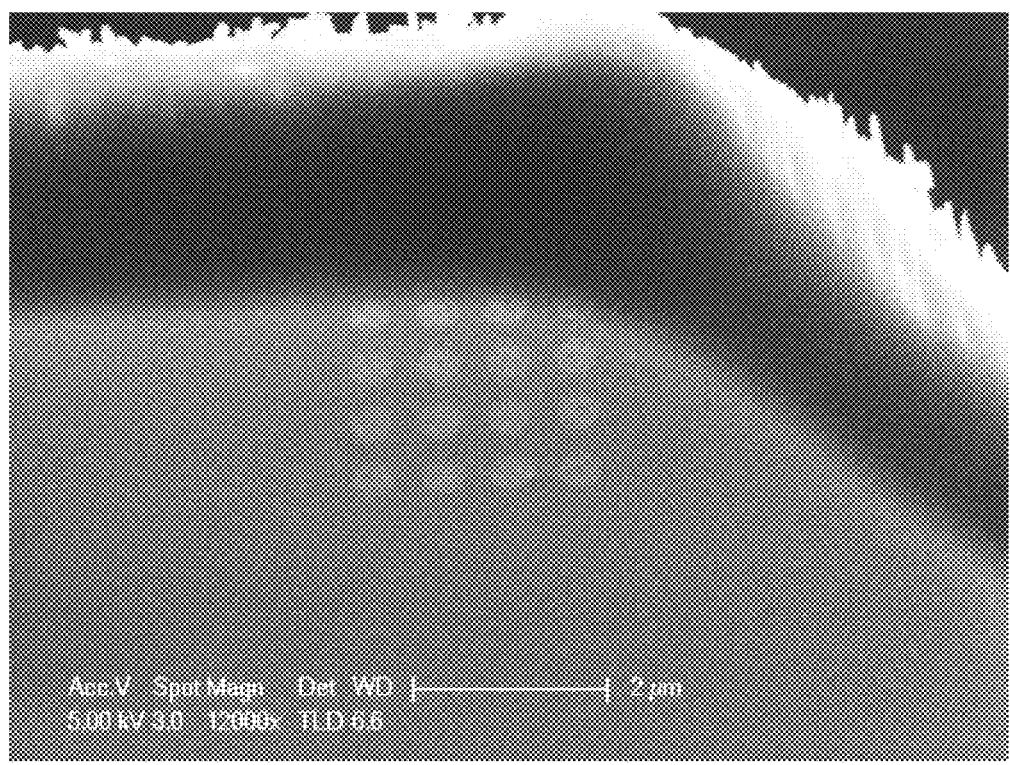
FIG. 6 shows vias within the integrated implantable device which can be used to provide connection between the electrodes and underlying electronics.

According to further embodiments of the present disclosure and with further reference to the etching of a top metal layer for deposition of a desirable electrode metal material, although the top metal (e.g. aluminum, copper, etc.) is etched (e.g. completely etched away), electrical connections of the deposited metal (e.g. Pt) can be made with the rest of the CMOS circuit through vias created through a corresponding CMOS processing which can be made of a different material (e.g. tungsten) and hence are not etched during the etching of the top metal layer (e.g. aluminum, copper, etc.). These vias, which can be made of a different conducting material, are shown in FIG. 6. The person skilled in the art readily understands that vias can be vertical metal connectors that connect the underlying circuitry to the top metal layer that is exposed (e.g. and etched away), as shown in FIG. 6. The 4 by 4 array of circles depicted in FIG. 6 are the vias that penetrate through a lower insulating layer (e.g. base on the well) and showing at a boundary of the etched area.

Usage of inherent structures created during the electronic chip fabrication as provided by the teachings of the present disclosure, using for example a CMOS process, in a post-processing step (e.g. creation of wells) as previously described and for functionalization of the electrodes, can result in a sensor which is fully integrated with the rest of the system (e.g. comprising electronics, vias, etc.). In turn, this can result in a higher manufacturing yield and reliability of the sensor and the system as a whole.

According to a further embodiment of the present disclosure, such sensors, either planar or patterned (e.g. comprising planar/patterned electrodes), can also be fabricated on the front side of the IC substrate. In an exemplary embodiment according to the present disclosure construction methods for metal structures available in CMOS technology can be used to fabricate such planar and/or patterned sensors. These can be combined with the construction steps related to the electronic IC, including connections between the sensor and the IC. In yet another exemplary embodiment according to the present disclosure, an exposed silicon area on the front surface can be used to fabricate such planar and/or patterned sensors during a post-processing step (e.g. after the CMOS processing step). According to yet another exemplary embodiment according to the present disclosure, planar and/or patterned sensors can be fabricated on a top metal layer, while the required electronics (e.g. IC) can be designed under the top metal layer (e.g. either fully or partially) to reduce the overall die area. In the case of the latter exemplary embodiment, spacing between the electrodes can be utilized to allow, for example, optical/RF waves, to reach optical/RF elements (e.g. integrated photovoltaic devices, RF antennae) which can be placed on a lower level below a level corresponding to the top metal layer. Such waves can be used to transmit/receive signals from/to the integrated device's electronic circuit. The person skilled in the art will know how to use such teachings according to the present disclosure for transmission/reception of other types of signals through regions of the top metal layer.

Figure 7:
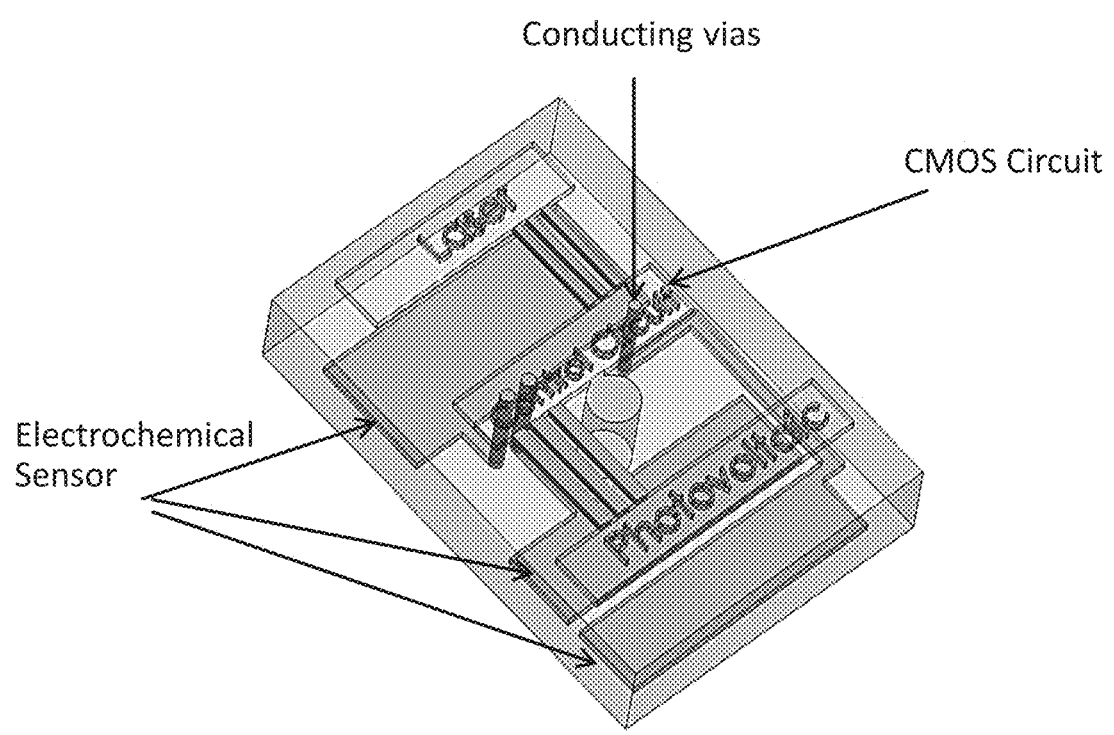
FIG. 7 shows an exemplary integrated implantable device.

According to an embodiment of the present disclosure the backside of an electronic integrated circuit (IC) substrate (e.g. fabricated via CMOS technology) can be used for fabricating such sensors (e.g. monolithically) which can then be connected to corresponding control circuits (e.g. signal processing) of the IC fabricated on the front side of the substrates using conducting traces, either through the substrate or from a side. FIG. 7 shows an exemplary embodiment according to the present disclosure where a sensor fabricated on the back side of a substrate is connected to an electronic IC fabricated on the front side of the substrate through vias created in the substrate.

According to further embodiments of the present disclosure such sensors can be fabricated separately from the corresponding electronic IC and bonded to the CMOS substrate of the IC at a later stage. Such bonding can be performed at a chip scale (e.g. one chip at a time) or at a wafer scale (e.g. several chips at a time). Different types of wafer bonding schemes known to a person skilled in the art can be used for this purpose.

The material constraints, such as metals/conductors used for the electrodes, can depend on a specific application. Noble metals and noble metal oxides can be used as electrode material for their stability. Platinum based metals can be used for their activity towards most of the metabolic species directly, such as in the case of $H_2O_2$ and $O_2$, or indirectly via an intermediate chemistry such as in the case of enzymatic sensing or polymer based sensing or sensing while functionalized using other chemistry. For example, oxygen, glucose detection can be done using such platinum based metals. Gold electrodes can be used for nucleic acid detection due to the ease of binding of gold through thiol bonds. Reference electrodes using, for example, Ag/AgCl material can be fabricated using known solid state fabrication methods which can readily support such material. Same material can be used for counter electrode as well. According to some embodiments of the present disclosure the working electrode and the counter electrode can be fabricated using a same metal and therefore simplify fabrication process. Choice of metal material for the counter electrode can be based on ability to sustain current so as to not limit working electrode current (e.g. size) and chemical compatibility of the metal material. Noble metals can satisfy both such requirements and less inert noble metals can be desirable in some circumstances (e.g. platinum can be more desirable over gold).

Figure 8A:
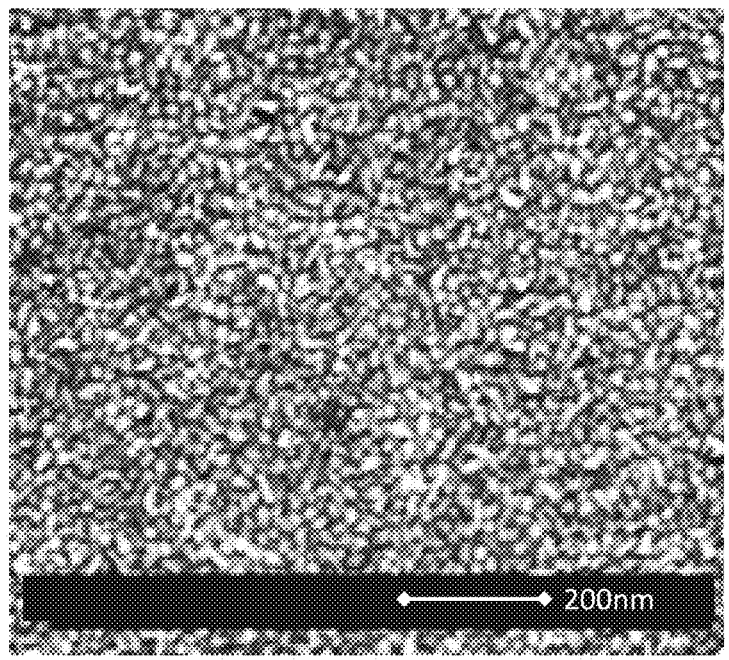
FIGS. 8A and 8B show scanning electron microscope pictures of a surface of a platinum (Pt) film and a platinum oxide (PtOx) film respectively.
Figure 8B:
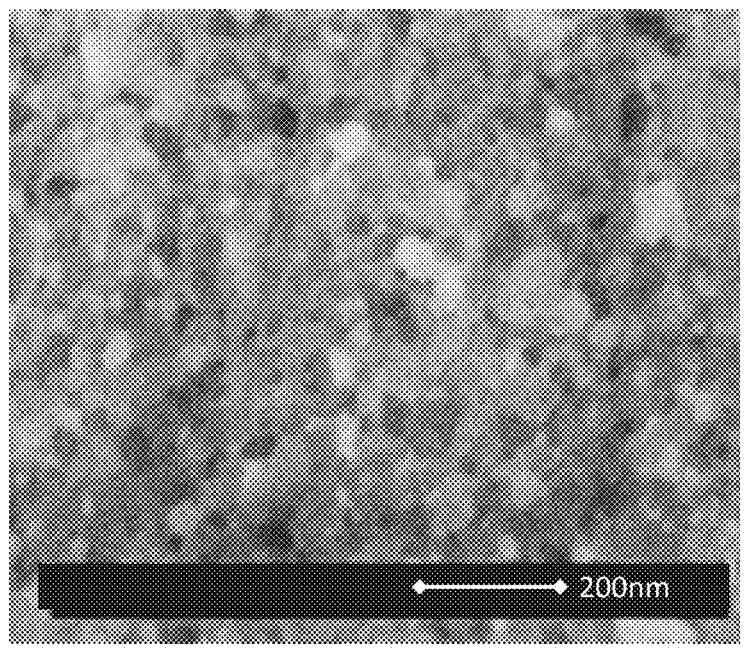

According to various embodiments of the present disclosure, the reference electrode material can be either Ag/AgCl based or noble metals (e.g. platinum (Pt), iridium (Ir), gold (Au), etc.) based materials. Ag can be deposited during a post-processing step of the integrated device and can be chlorinated using either chlorine plasma or by dipping it in a chloride solution (e.g. hydrochloric acid), or electrochemically in a solution containing chloride ions (e.g. hydrochloric acid). Pt based or other noble metals based reference electrodes can help avoid the use of other materials (e.g. silver Ag) and hence can make the post-processing step simpler. Since Pt itself is sensitive to pH and peroxide interference, in some cases, such as glucose sensing, it can be unstable for usage as a reference electrode. However, coating such reference electrode with a suitable insulating layer can increase its stability. For example, a somewhat inert layer of Platinum Oxide (PtOx) can be used to make a combined Pt/PtOx reference electrode. According to an exemplary embodiment of the present disclosure a Pt/PtOx working and/or counter electrodes can be fabricated by oxidizing a Pt layer of the electrodes electrochemically or by depositing oxidized platinum on the electrodes. The former method can eliminate a need for an additional deposition step which can be beneficial in reducing manufacturing cost, time and complexity. Using a same material for both the working and the counter electrodes can be desirable since it can avoid the need of having an additional material (e.g. Ag) and/or using other types of electrodes (e.g. hydrogen-based, mercury-based, etc.) which may need special post-processing and may also be toxic (e.g. Ag, AgCl). It should be noted that Pt based reference electrodes can be used in harsh conditions where reference electrodes made of Ag/AgCl may not be feasible, although simple Pt may be better in such extreme conditions. Since Pt is a noble and very inert material, it is not easy to oxidize even with strong oxidizers such as hydrogen peroxide. Applicants of the present disclosure have attempted oxidation of Pt electrodes (e.g. reference electrode fabricated on the integrated sensor) using strong oxygen plasma as well as using strong oxidizing agents (e.g. sulfuric acid) along with high electrochemical voltages applied to the Pt. Oxygen plasma exposure showed some effect on the Pt surface and corresponding electron diffraction x-ray studies showed some oxygen as part of a film on the surface of the Pt. The films were subsequently heated to release any oxygen physically adsorbed in the films. Attempts in determining the chemical nature of the oxide film were inconclusive. Nonetheless, the resulting electrochemical stability suggested that the film (e.g. as formed on the surface of a Pt reference electrode upon oxidation under oxygen plasma and heating to remove absorbed oxygen while not affecting operation of the underlying electronic system) had become a better reference electrode material than bare Pt. SEM's (e.g. via scanning electron microscope) of such films are shown in FIGS. 8A and 8B, former figure depicting a Pt based film and latter figure a PtOx based film obtained via the mentioned steps of oxygen plasma exposure followed by heating.

Figure 9:
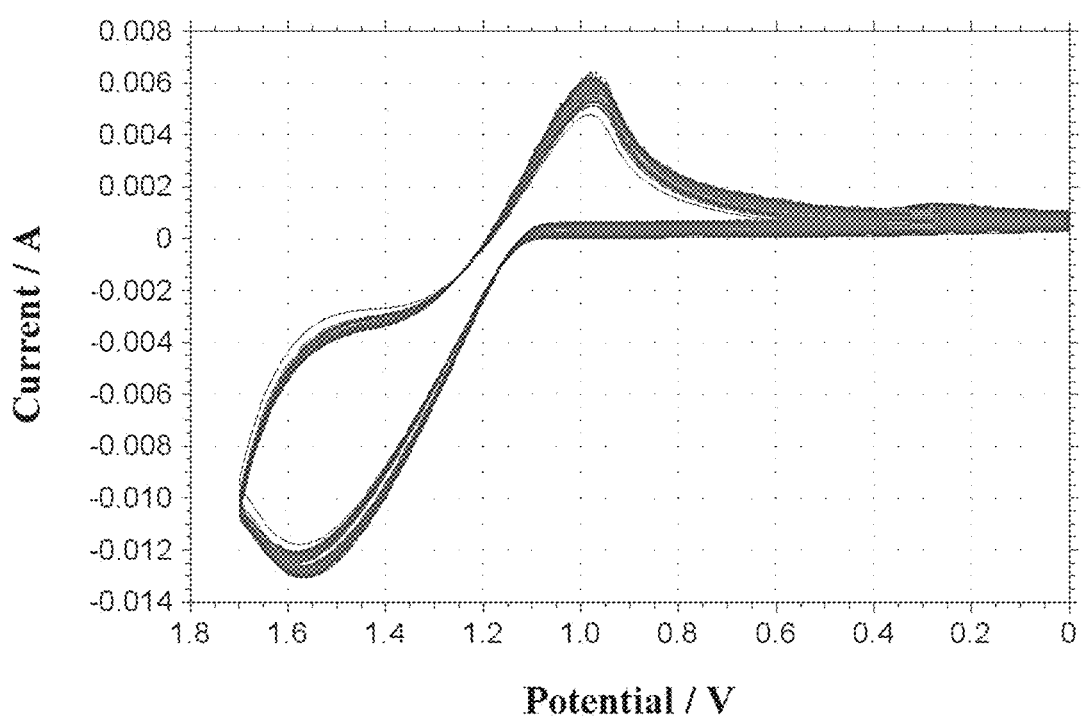
FIG. 9 shows an exemplary electrochemical oxidation curve (current versus voltage) of platinum in a sulfuric acid solution.
Figure 10A:
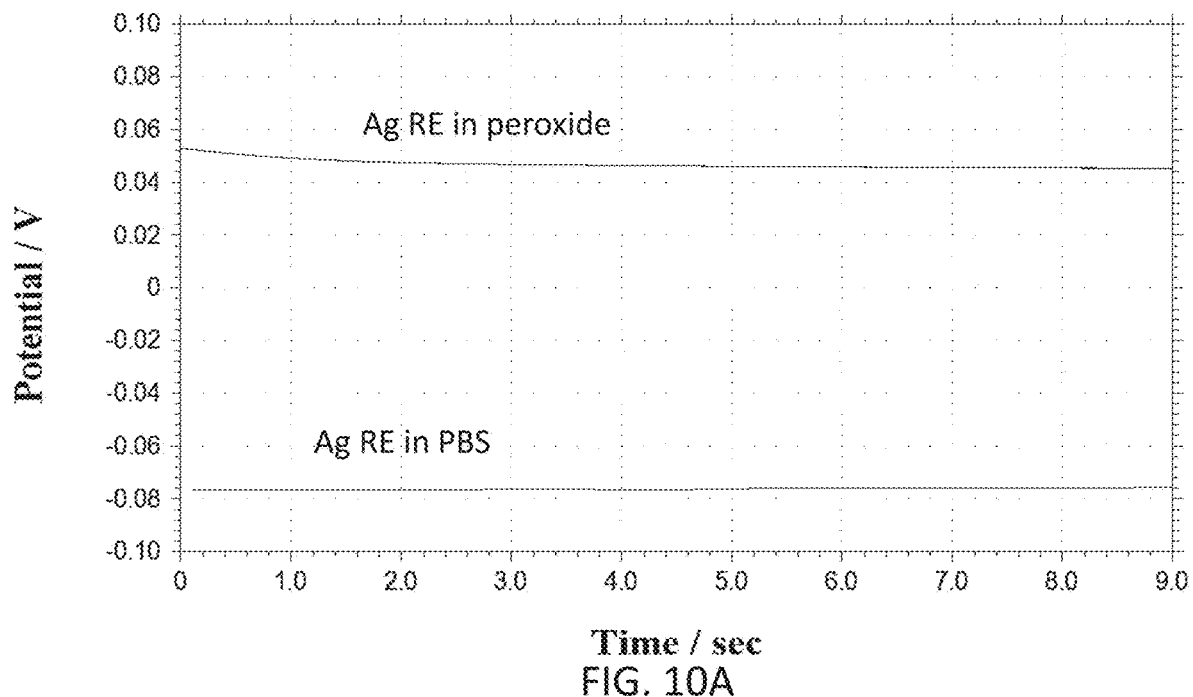
FIGS. 10A-10D show various graphs representative of open circuit test for electrode (e.g. reference electrode RE) temporal stability and interference effects in peroxide solution.
Figure 10B:
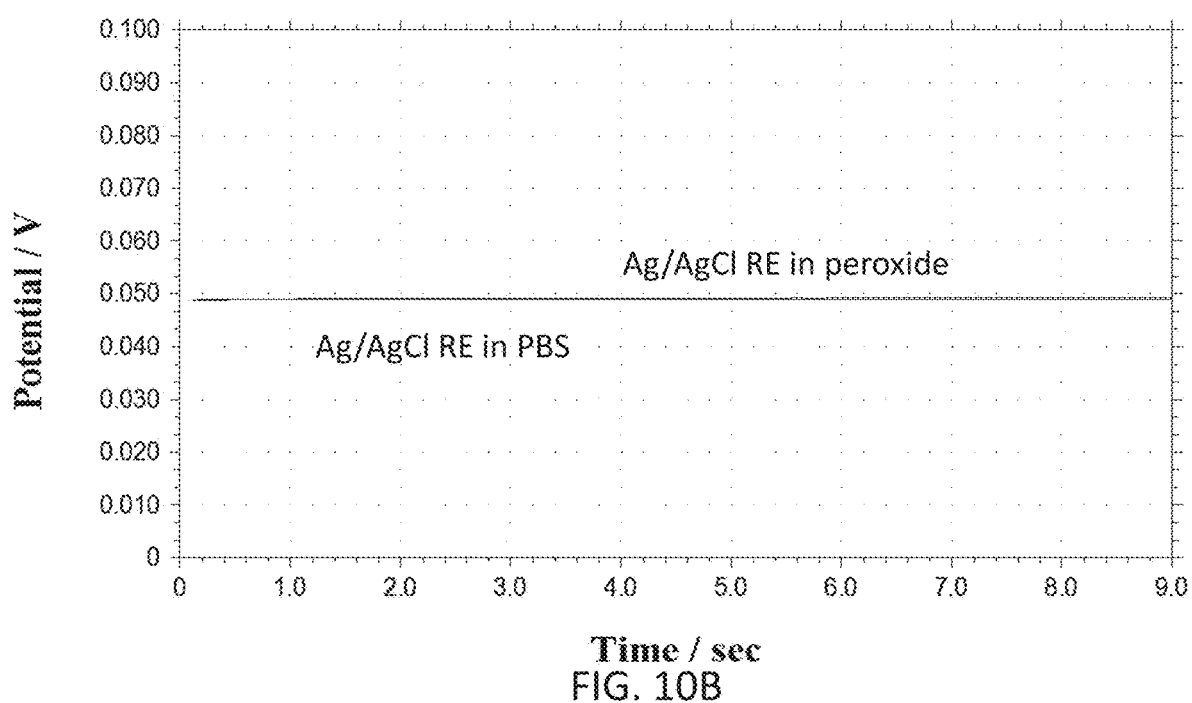
Figure 10C:
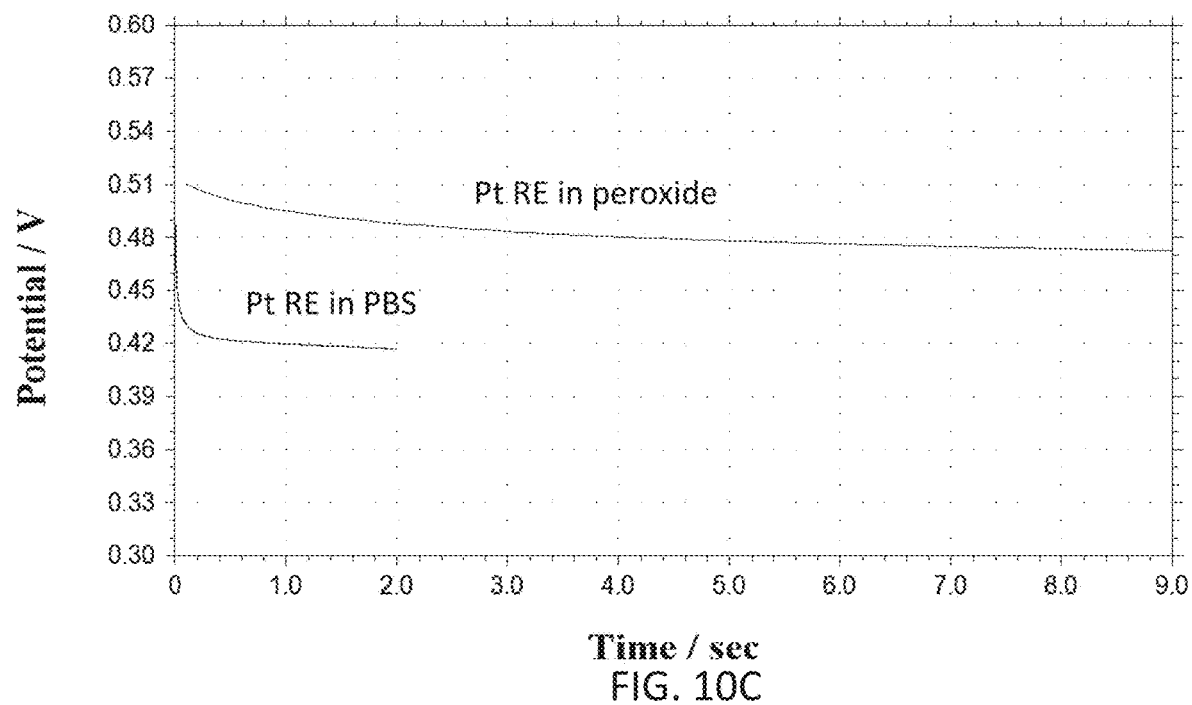
Figure 10D:
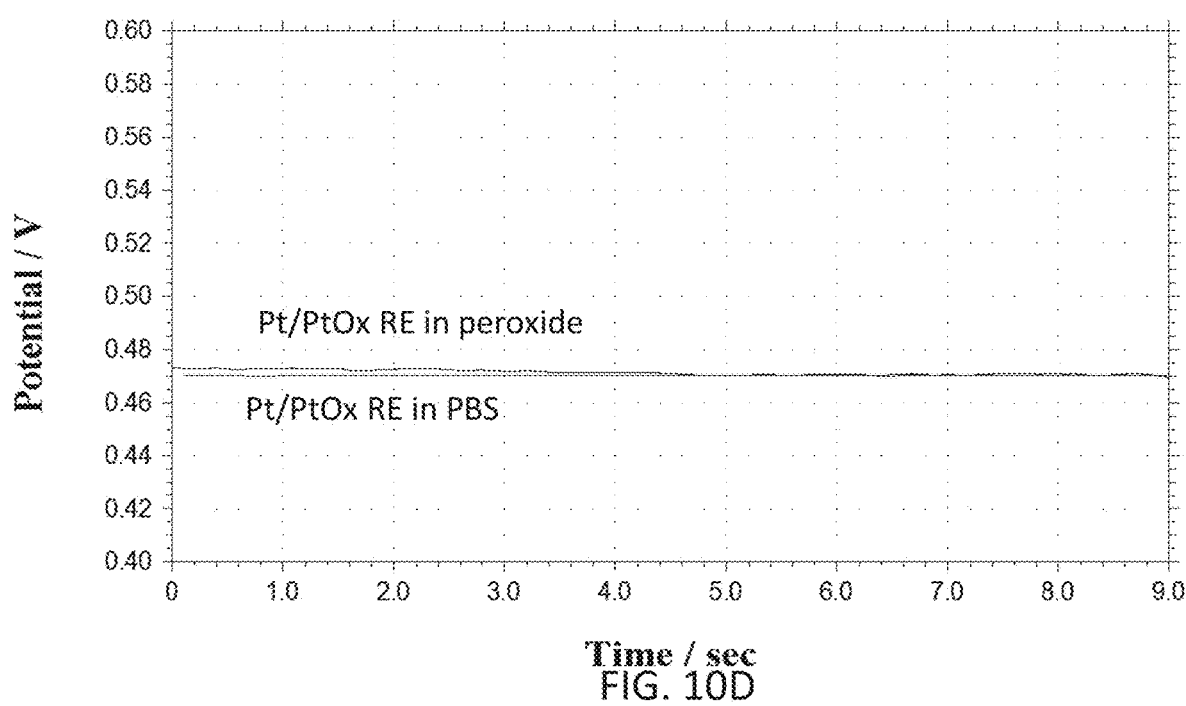

According to further embodiments of the present disclosure noble metal/noble metal oxide electrodes can be used as reference or working electrodes depending on a desired application. Noble metal/noble metal oxide electrodes can be fabricated using cleanroom procedures, e.g. via deposition under oxygen plasma, or chemically, such as with electrochemical oxidation in a mixture of strong oxidizers which can include sulfuric acid and hydrogen peroxide (e.g. FIG. 9). Applicants of the present disclosure have developed special operating parameters for said deposition techniques such as usage of such techniques for deposition of noble material on the integrated electrodes do not damage the underlying circuitry (e.g. fabricated for example via CMOS methods). FIG. 9 shows an exemplary electrochemical oxidation curve (current versus voltage) of platinum in a sulfuric acid solution (e.g. 0.1M (molar concentration in phosphate buffered saline (PBS)) used for fabrication of noble metal/noble metal oxide integrated electrodes. FIGS. 10A-10D show various graphs representative of open circuit test for electrode (e.g. reference electrode RE) temporal stability and interference effects in peroxide solution. These are summarized in the table below.

| Electrode Material | Temporal Stability (voltage change) | Peroxide Interference (voltage change) |
|---|---|---|
| Ag | 15 mV | 120 mV |
| Pt | 30 mV | 60 mV |
| Ag/AgCl | 5 mV | 3 mV |
| Pt/PtOx | 20 mV | 10 mV |

According to an exemplary embodiment of the present disclosure, a deposition under oxygen plasma technique can be used to produce a noble metal/noble metal oxide reference electrode on the sensor. This eliminates the need to use a wet electrochemical post processing step. According to an alternative embodiment of the present disclosure an electrochemical oxidation technique can be used in order to produce a metal/metal oxide electrode, such as Pt/PtOx. Such electrochemical oxidation technique can be done in a mixture of sulfuric acid (e.g. strong oxidizer) at a concentration of 1-2 M and hydrogen peroxide (e.g. strong oxidizer) at a concentration of 0.5-2 M dissolved in phosphate buffer saline (which can provide a source of chloride ions for Ag/AgCl reference electrode stability). The Pt electrode can then be oxidized by subjecting it to high oxidative and low reductive potentials repeatedly (e.g. alternating). The high oxidative potential can oxidize the Pt layer of the electrode while the low reductive potential can polish the oxide layer for increased stability of the layer. In one exemplary embodiment the high oxidative potential can be 2.5 V with respect to Ag/AgCl reference potential and the low reductive potential can be 0.5 V with respect to the same reference potential. In an alternative embodiment of the present disclosure, the electrode can be oxidized galvanostatically by subjecting in to determined oxidative and reductive currents repeatedly, with same effects as mentioned with respect to the high oxidative and low reductive potentials. Those skilled in the art can readily extend these teachings according to the present disclosure and use in other electrochemical techniques. Stability of electrodes fabricated using such techniques were characterized by the applicants of the present disclosure by measuring open circuit potential of the Pt/PtOx electrode with respect to a Ag/AgCl reference electrode over time, as depicted in FIGS. 10A-10D and above table. The electrochemical oxidation technique herein presented can be performed at room temperature (e.g. 24 degrees Celsius) as well as any temperature range between 10 degrees and 100 degrees Celsius (e.g. solution in liquid form). A higher temperature can provide for a quicker oxidation of the metal.

Interface properties (e.g. surface) of the electrodes can be controlled by control of material deposition onto the electrodes to promote a desired reaction. This can increase the reaction rate as well as transduction of the signal from the functionalization chemistry. Furthermore, this can be optimized to stabilize the immobilization matrix (e.g. hydrogel) for long term applications.

According to some exemplary embodiments of the present disclosure, the electrode surfaces can be formed or modified in order to promote desired reactions. Some deposition techniques and rates can provide a rougher surface that can increase surface area and thus current. Grain formation can be encouraged or discouraged in the metal layers, as grain boundaries can allow the solution to penetrate through the top metal layer to some extent and interact with the lower layers, which can be desirable, for instance in Ag/AgCl reference electrode, or undesirable, as in the Pt electrodes with less inert metals (such as titanium (Ti), tungsten (W), copper (Cu), etc.) underneath.

According to further embodiments of the present disclosure, the surface of the electrode can also be made more hydrophilic, for instance by applying a high voltage plasma (e.g. a technique colloquially referred to as just zapping), or by using an oxygen plasma either during or after deposition. This can enable hydrophilic substances to adhere better on the electrode surface, such as, for example, an immobilization matrix (e.g. a gel containing reaction enzymes which can immobilize the enzyme and prevent it from leaching into the analyte (e.g. blood or interstitial fluid)). The person skilled in the art readily appreciates the various teachings according to the present disclosure which allow flexibility in electrode surface characteristics as to provide a hydrophobic or a hydrophilic electrode in an integrated electrochemical device.

Figure 11:
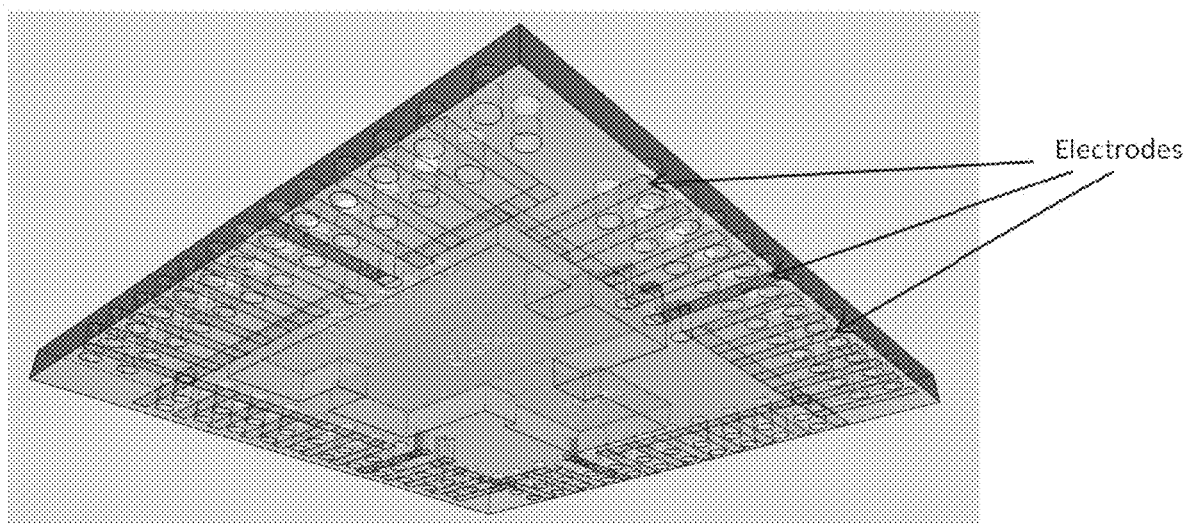
FIG. 11 shows an exemplary integrated implantable device according to an embodiment of the present disclosure whose sensor has distributed electrodes.

In some cases it can be desirable for an integrated system (e.g. integrated electrochemical sensor) to have some special functional patterns such as, for example, through holes for fluid flow. It follows that according to an embodiment of the present disclosure the electrodes are designed around such functional patterns in a distributed manner. Distributed electrodes, as depicted in FIG. 11, can provide an increase in signal quality (e.g. of the interface reaction) due to the distributed nature of a corresponding analyte solution. Design of distributed electrodes can be done utilizing fractal mathematics to optimize signal to noise ratio while considering the distributed nature of the analyte solution. In the exemplary embodiment according to the present disclosure depicted in FIG. 11, the distributed electrodes are shown on the back side of an integrated device so as to utilize the entire available die area, and are connected to the electronics on the front through corresponding vias and connections (not shown). Alternative embodiments can be provided where the distributed electrodes are designed on the front side of the integrated system (e.g. same as the electronic IC).

It should be noted that although the exemplary distributed electrodes configuration depicted in FIG. 11 shows electrode components of a substantial same geometry (e.g. length and width), the teachings according to the present disclosure allow the person skilled in the art to adapt corresponding distributed electrodes geometries to particular design and functional constraints of the integrated device. For example, the electrodes can be designed to be long and narrow rectangles for a case where a long rectangular device is desired, or can be square for a case where a square device is desired. Same design rules as presented in the previous sections of the present disclosure for design of non-distributed electrodes can be applied to the design of distributed electrodes as well.

Sensor Fabrication:

Fabrication of fully integrated electrochemical devices according to the various embodiments of the present disclosure must be performed in a manner to avoid damage to the various underlying system and components of the device, such as, for example, the electronic IC which can be fabricated using known CMOS related methods, and/or other related system components. In follows that various fabrication methods according to further embodiments of the present disclosure which reduce damage to the underlying system and components thereof are presented in the following sections.

For planar sensors, spray-coating based lithography can be used in cases where corresponding device dies are small, or cases where a corresponding edge bead (e.g. accumulation of resist at the edge of a die) is significant or cases where a corresponding surface morphology does not allow proper spinning of resists. Standard lithographic patterning can be achieved in other cases. It should be noted that the surface of the electronic substrates may not be completely planar, and therefore resists which can provide enough thickness to result in a conformal coating can be used. According to some embodiments of the present disclosure, high power/long duration temperature and Ultraviolet/e-beam exposure can be avoided during the lithographic patterning. This can be done, for example, by using resists which can achieve lithographic patterning in short duration with moderate dosages.

For isolation of the sensor with respect to other components of the integrated device, high temperature and long duration thermal oxidation techniques, which can damage the underlying electronics, can be avoided in favor of low-temperature and short duration deposition based techniques. Such low-temperature and short duration deposition techniques can be used to deposit desired isolation materials. For example, CVD based techniques instead of thermal oxidation can be used to isolate portion of the substrate material (e.g. silicon) used for sensor fabrication from substrate material used for the other components of the integrated device (e.g. electronics). In general, the various processes and methods according to the various teachings of the present disclosure can be performed at temperatures between 10 and 200 degrees Celsius such as not to damage the underlying electronics.

Similarly, low temperature deposition techniques, such as, for example, sputtering and electron beam deposition, can be used to deposit different materials desired for fabrication of the sensors. Avoiding high temperature thermal deposition during fabrication of the sensors can in turn reduce damage to the electronic substrate and related components.

Aligned Photolithography and electron beam lithography can be used to create micro and nano scale structures on the sensor electrodes, for cases where patterned electrodes are desired. Dummy patterns can be fabricated during the CMOS fabrication process to act as alignment marks for fabrication methods of such patterned electrodes. The Lithographic methods for fabrication of the patterned sensors can be done at a wafer scale during the electronics fab (e.g. CMOS) phase or at a die scale after the wafers are received from the fab and processed. The wafer level processing of patterned sensors can decrease overall production cost of the integrated device and can increase a corresponding yield.

Sensors according to the various embodiments of the present disclosure can be used in implantable integrated devices. In order to reduce complexities after implantation, the sensors can be covered with biocompatible materials. This can be done by depositing such biocompatible materials using, for example, vacuum based deposition or simple dip-coating type methods.

Functionalization

Figure 12A:
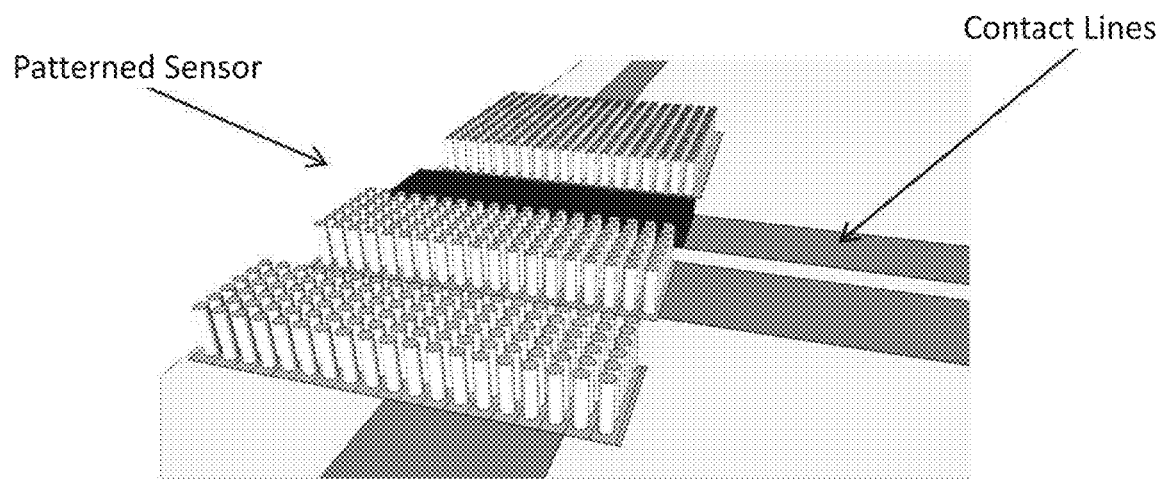
FIGS. 12A and 12B show an exemplary sensor of the implantable integrated device with distributed electrodes prior to functionalization and after functionalization respectively.
Figure 12B:
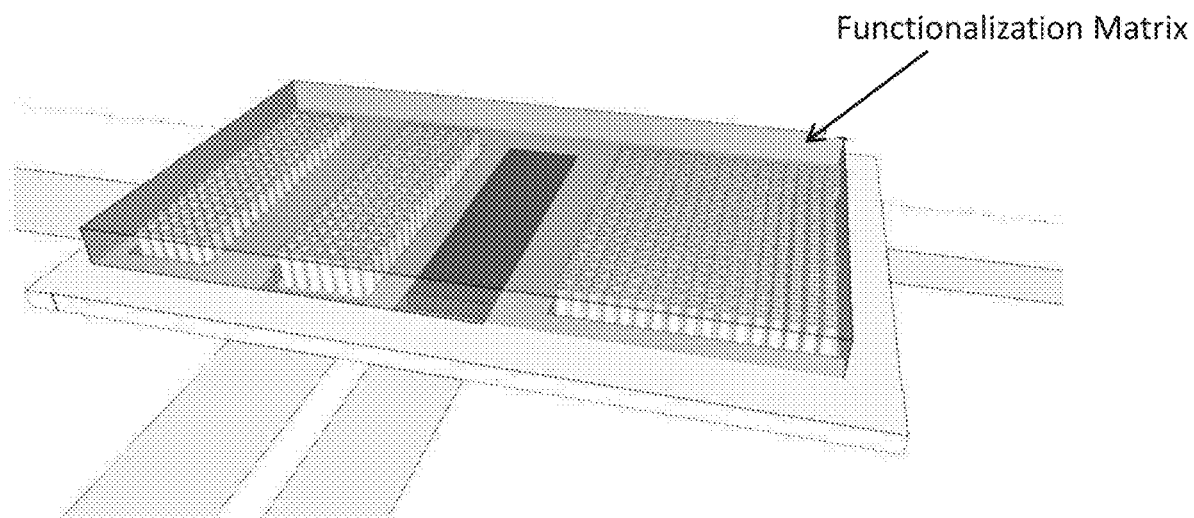

Functionalization of sensors according to the various embodiments of the present disclosure can be performed so as to make these sensors selective to different species. Such functionalization can be done either in situ or ex situ. FIG. 12A shows an exemplary sensor with distributed electrodes prior to functionalization. An exemplary resulting configuration of the sensor depicted in the FIG. 12A with a functionalization matrix is shown in FIG. 12B.

In-Situ functionalization can allow for an easily integratable process. For small dies, spotting and dip coating can be used for applying a functionalization matrix. According to an embodiment of the present disclosure, a single step functionalization can be performed by spin coating at wafer level before dicing the final dies. Such single step functionalization can increase uniformity and repeatability performance of the functionalization.

Well structures according to the various embodiments of the present disclosure formed in the CMOS sensor (e.g. during a CMOS post-processing phase) can be advantageously used during the functionalization phase. Individual dies can be functionalized by injecting liquid hydrogel mixture, for instance using a fluid dispensing robot, into wells on the CMOS sensor formed in post-processing. Wafer-scale functionalization can be performed using a fluid dispensing robot, as well as via spin or spray coating of the wafer, stencil coating, or whole wafer coating followed by stencil protected removal, for instance via oxygen plasma. Using spin or spray coating, leveraging the form factor advantages the wells provide, and protected subtractive gel patterning, are novel techniques according to the various embodiments of the present disclosure that enable cost-effective wafer-scale production for the presented integrated electrochemical sensors.

Functionalization Versatility

The Chemistry used for functionalization of the integrated electrochemical sensors according to the teachings of the present disclosure can be versatile and hence can lead to a variety of applications. Since the underlying CMOS circuitry can be modified/adapted to perform a variety of electrochemical sensing tasks, and since each sensing task can be functionalized with an array or variety of chemistries, the applications of the sensors according to the present teachings can be innumerable. Some exemplary applications are presented below.

The sensor can also be functionalized with any oxidoreductase to detect electron transfer, or peroxide concentration, or oxygen concentration, or any other change resulting from enzyme interaction with an analyte. For instance lactate oxidase can be used to sense lactate. Applicants of the present disclosure have used glucose oxidase, glucose dehydrogenase, and their mixtures with horseradish peroxidase in order to achieve glucose sensing. For the case of enzymatic sensing, following examples illustrate this point further.

For renal sensors, following enzymes can be used instead of glucose oxidase: uricase (uric acid), urease, ascorbate oxidase, and sarcosine oxidase (e.g. creatinine)

For liver function testing, following enzymes can be used: alcohol oxidase and malate dehydrogenase.

Other notable enzymes can include glucoamylase, glutamate oxidase and cholesterol dehydrogenase.

For physical stress and similar sensing functions, lactate oxidase can be used.

Integrated electrochemical sensors according to the various teachings of the present disclosure can be used for sensing mechanisms other than amperometric sensing. For example, such integrated electrochemical devices can be used for electrochemical impedance measurement, or even for stress sensing using cortisol level (e.g. as a level of cortisol hormone can rise during psychological stress) in people with stress management issues. The person skilled in the art readily appreciates the flexibility provided by the presented integrated electrochemical sensor and can use the present teachings to produce integrated sensors and corresponding circuitry for specific applications.

Exemplary Case 1: Fully Wireless Implantable Sensing Device

In this section of the present application an exemplary system design case using the fully integrated electrochemical sensor device presented in the previous sections of the present application is provided. The exemplary design according to the various embodiments of the present disclosure as presented in this section is a miniaturized fully implantable continuous (e.g. real-time and always available) health monitoring microsystem on a CMOS platform. The proposed design incorporates electrochemical sensing techniques as presented in the prior sections of the present application using an ultra-low-power electronics as the underlying electronics. It can be wirelessly powered through an electromagnetic wireless link and can support bidirectional data communication with an external transmitter/reader device (e.g. reader) through the same wireless link. A low-power potentiostat is used to interface with the on-chip sensor (e.g. electrodes) and an ADC record the on-chip sensor readout. Dynamic range of the ADC can be programmable via wireless configuration data sent to the wireless sensor device. Functionalized integrated electrodes, as per the teachings of the various embodiments presented in the previous sections of the present disclosure, are used to enable a specific measurement, such as, for example, glucose level body fluids. Applicants of the present disclosure have fabricated a prototype of the presented wireless implantable sensing device in CMOS technology and were successful in validating such device for complete wireless operation in a tissue. The sensing capability of the implanted device was tested using glucose measurements as an example.

The fully-integrated wireless sensor platform (e.g. system) presented wherewith, is at reduced size scale (near millimeter scale in larger dimensions) compared to current state-of-the-art systems. Multiple unique features of the presented system allow such reduction in size. First, power transfer and data telemetry is performed using an optimized integrated electromagnetic wireless link without using a large size antenna. Furthermore, using the various teachings in the previous sections of the present disclosure, the sensor is realized using miniaturized integrated electrodes acting as an electrochemical sensor after suitable functionalization. An ultra-low power and ultra-small scale potentiostat is designed to control the sensor operation. This is followed by an ultra-low power and ultra-small ADC which converts the analog sensor signal into digital domain. The overall power consumption of the implant is minimized by using ultra low power and minimal number of components in the electronics as well as by using ultra-low power communication link (e.g. modulation scheme) between the implant and an external transmitter/reader. The prototype demonstrates the feasibility of drastically miniaturizing implantable sensing systems which can conceptually enable their application in making clinically accurate measurements in many areas. The applicants of the present disclosure have proved such concept by implementing a CGM type prototype system as implementation of such system can be challenging as well as useful in the healthcare industry. The prototype system is fabricated in 0.18 μm CMOS technology but is not limited by this technology in any way. The sensor is implemented using the top metal in the CMOS process using post-processing (e.g. as described in previous sections of the present disclosure) thus avoiding the need of bonding external sensors to the electronics and hence achieving minimal size and power consumption. Therefore, in the prototype system, the sensor and the underlying electronics are located on a same face of the integrated device, although according to the teachings of the present disclosure such sensor can be also placed on a face opposite to the top face.

Figure 13:
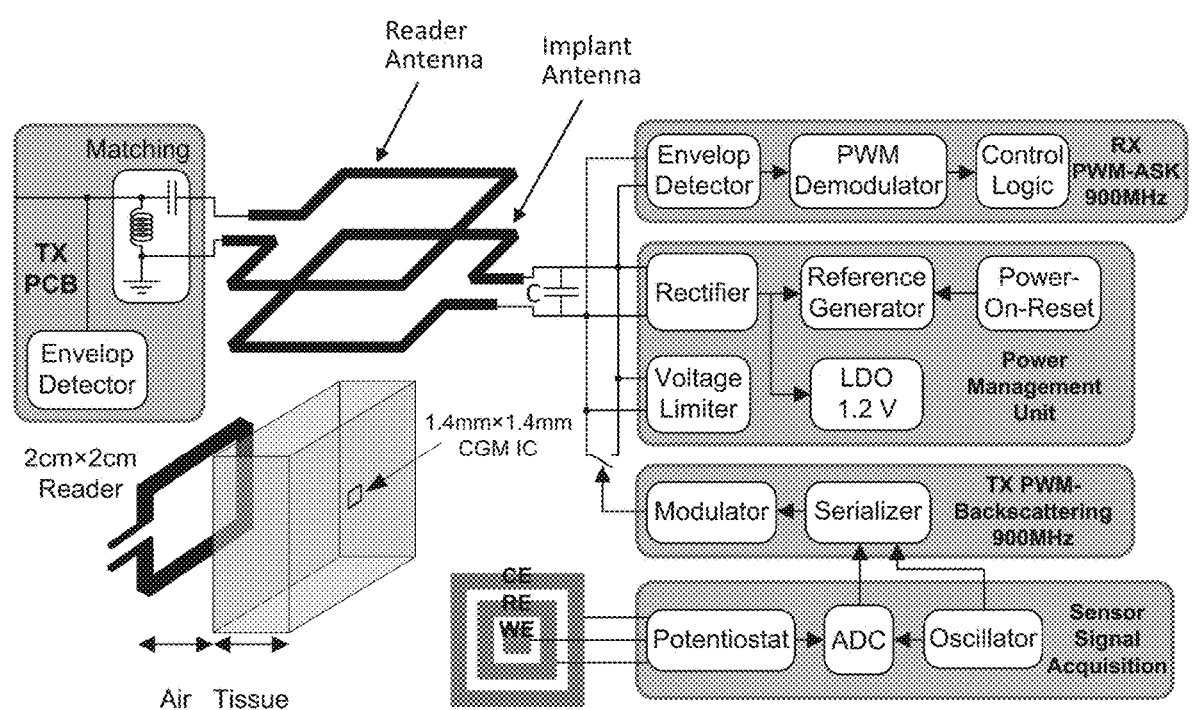
FIG. 13 depicts a block diagram of a system comprising the implantable integrated device, a corresponding external transmitter/reader and an interface region between the two.

FIG. 13 shows a block diagram of the wireless implantable sensing device according to an exemplary embodiment of the present disclosure. It consists of integrated electronics to control sensor operation (labeled sensor signal acquisition), a power management system (labeled power management unit) to power the whole system, a transmit system to communicate the data to the external transmitter/reader (labeled TX PWM-backscattering 900 MHz), a receive system to receive commands from the external system (labeled RX PWM-ASK 900 MHz), an integrated three electrodes based electrochemical sensor (labeled WE, RE, CE for working, reference and counter electrode respectively) and an electromagnetic wireless link for both power and communication (labeled implant antenna).

According to an exemplary embodiment of the present disclosure, the electromagnetic wireless link through which power is provided to the implantable sensing device and which is also used as a bi-directional communication link, can be an inductive coupling link designed to operate in the industrial, scientific and medical (ISM) radio band at a frequency close to 900 MHz (e.g. 902-928 MHz), which can be employed in the exemplary wireless implantable device so as to minimize loss inside tissues [e.g. reference 4, herein incorporated by reference in its entirety]. The person skilled in the art readily understands that the choice of the frequency can depend upon many factors and can therefore be different for different applications. Furthermore, the wireless link does not need to be an inductively coupled link (e.g. near-field) as an RF link with far-field powering and communication can also be used.

At the chosen frequency band, an on-chip resonant system consisting of an inductor (e.g. L) and capacitor (e.g. C) can be used to resonate with an external LC system at a matching resonant frequency. The on chip coil (e.g. antenna) can be implemented using the top metal (e.g. fabricated via CMOS process) or a combination of metal layers depending upon application and thickness of metal layers. For instance, a relatively thick top metal layer of thickness about 4 μm to 5 μm may be sufficient for fabricating the coil, such as the case for the prototype implantable device the applicants of the present disclosure fabricated (e.g. top metal layer about 4.6 μm thick). In other cases such thickness may not be sufficient or a top metal layer may not have such thickness, and therefore several metal layers can be stacked to provide a desirable thickness for fabrication of the coil. In a preferred embodiment, for a given size of the on chip coil (e.g. available surface space), an associated inductance as well as quality factor can be maximized. For inductive links, an on-chip capacitor can be used together with the inductor of the on chip coil to create an LC resonant system. In one example, the applicants of the present disclosure used a thick top metal available in a commercial CMOS process (e.g. TSMC 0.18 μm process) to make a 4 turn coil which occupies 1.3×1.3 mm². A 400 fF on-chip metal-insulator-metal (MIM) capacitor (e.g. labeled C in FIG. 13) is used to resonate with the coil at the selected frequency (e.g. close to 900 MHz). The person skilled in the art readily appreciates the small form factor of the LC resonant system presented which can be used to wirelessly power the implantable device.

Figure 14:
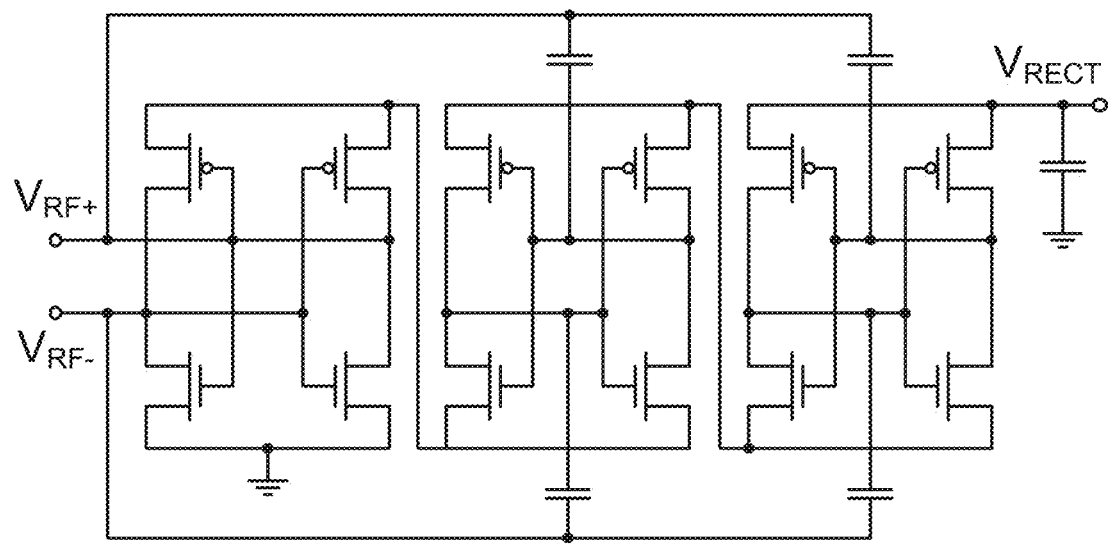
FIG. 14 depicts a circuit diagram of an exemplary 3-stage self-synchronous full-wave rectifier.
Figure 15:
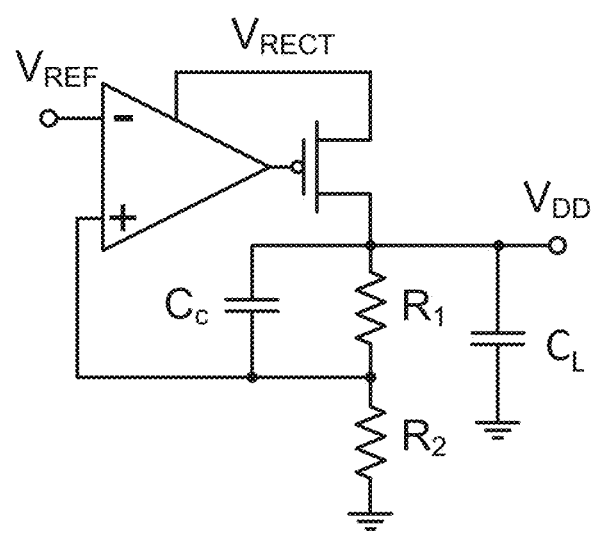
FIG. 15 depicts a circuit diagram of an exemplary linear voltage regulator.
Figure 16:
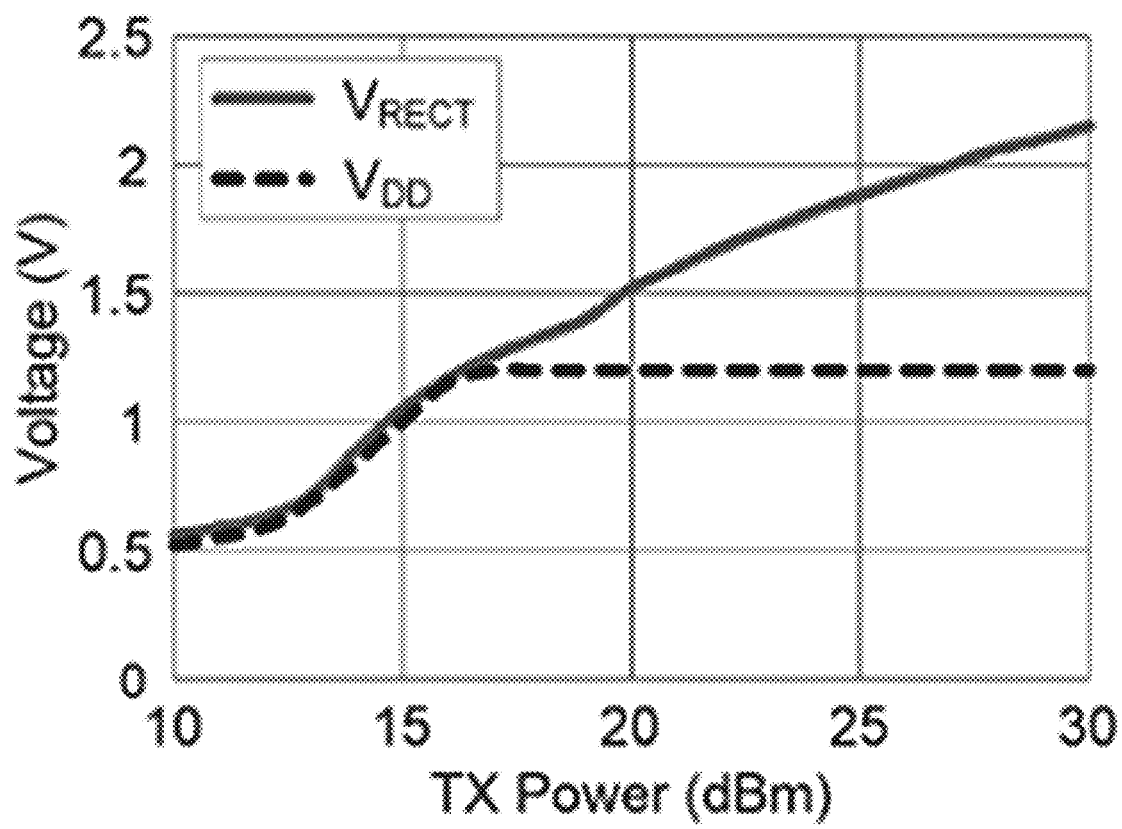
FIG. 16 shows a graph representative of measured rectifier and regulator output voltages at 6 µW load versus transmitted power to the integrated implantable device at 7 mm separation between the external transmitter/reader device and the implanted integrated implantable device.

A high frequency signal (e.g. at the selected frequency) that the resonant system receives is converted to DC using an efficient rectifying circuit. For example, in their prototype implementation, the applicants of the present disclosure used a 3-stage self-synchronous full-wave rectifier followed by a 400 pF MOS capacitor to filter a resulting ripple, as shown in FIG. 14. Simulation data have shown that such rectifier, as depicted in FIG. 14, can have an efficiency of 60%, as measured by power received by the on-chip LC system to power output by the rectifier. Based on the rectified output $V_{RECT}$, a voltage reference (e.g. $V_{REF}$ of FIG. 15) and a linear voltage regulator circuit (e.g. FIG. 15) are used to create a stable supply voltage $V_{DD}$ at a desired level for operation of the various subsystems. Such voltage level can depend upon factors of the overall design. For the exemplary prototype system presented herein, a stable 1.2V supply voltage VDD using an efficient voltage reference in conjunction with a reference voltage generator (e.g. as shown in FIG. 13) is generated. The voltage regulator, as depicted in FIG. 15, is designed to have improved stability and reduced power consumption. As an example, a capacitor Cc of FIG. 15 is used to introduce a zero in a frequency response plot of the voltage regulator circuit and therefore help with the stability of the regulator. Filtering is also performed on the regulated voltage $V_{DD}$ to further ensure stability and to reduce high frequency supply noise. As an example, such filtering can be provided by an on-chip MOS capacitor $C_L$ of FIG. 15. For the exemplary prototype system, such capacitor value can be 550 pF. A voltage limiter can also be employed so as to avoid excessive voltage at the rectifier output to protect system integrity. Although not shown in FIG. 13, such voltage limiter can be provided at the output of the rectifier. The power supply described in this section can generate reasonable power with suitable separation (e.g. distance) between the external resonant system and the implanted device. As an example, measured rectifier and regulator output voltages at 6 μW load versus transmitted power at 7 mm separation between the external transmitter/reader and the implant (e.g. implanted device) are shown in FIG. 16. The person skilled in the art readily appreciates the low power consumption system (e.g. 6 μW) presented in this section to perform the power management task of the implantable device.

Figure 17:
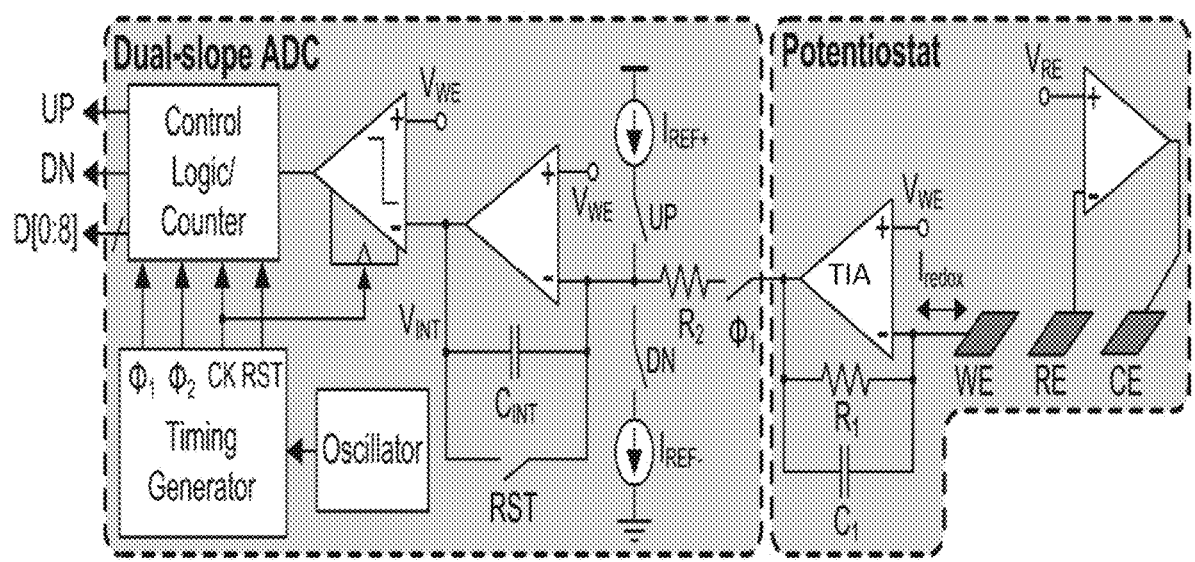
FIG. 17 shows an exemplary embodiment of an acquisition system used in the implantable integrated device.

The sensor signal acquisition system can comprise a readout circuitry including a potentiostat to maintain the required redox potential between the working (WE) and reference (RE) electrode while supplying current through the counter (CE) electrode using a feedback amplifier as shown in FIG. 17. The potentiostat can be employed in different electrochemical modes to detect glucose. According to some embodiments of the present disclosure the potentiostat can work in both amperometry and cyclic voltammetry regime for glucose detection and can support a wide range of voltage difference between the working and reference electrode while covering a large current range as well. The current from the potentiostat is converted into digital domain using an n-bit (excluding the sign bit) dual-slope ADC with an on-chip integrating capacitor, $C_{INT}$. In order to enable bidirectional current measurement (e.g. communication from the external transmitter/reader to the implant and from the implant to the external transmitter/reader), a trans-impedance amplifier (TIA) with resistive feedback can be employed at the front-end as an interface between the working electrode and the dual-slope ADC, as depicted in FIG. 17. Another on-chip capacitor Ci can be used to further reduce TIA noise. The TIA can also prevent injection of the ADC switching noise into the sensor working electrode.

Figure 18A:
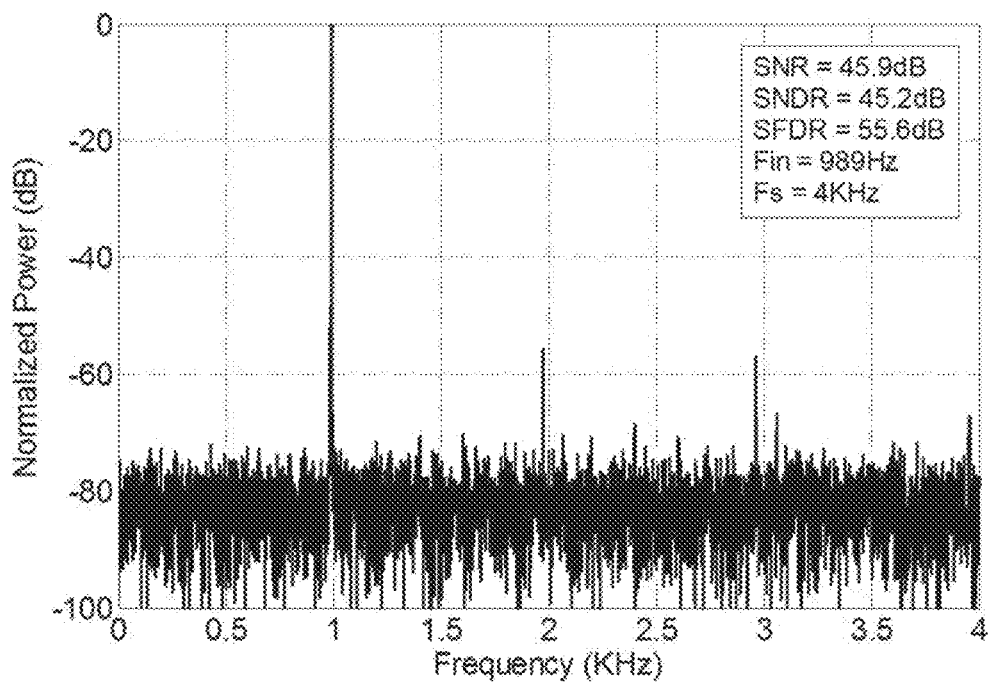
FIGS. 18A and 18B show graphs representative of a performance of a dual-slope 8 bit ADC (excluding sign bit) used in the acquisition system depicted in FIG. 17.
Figure 18B:
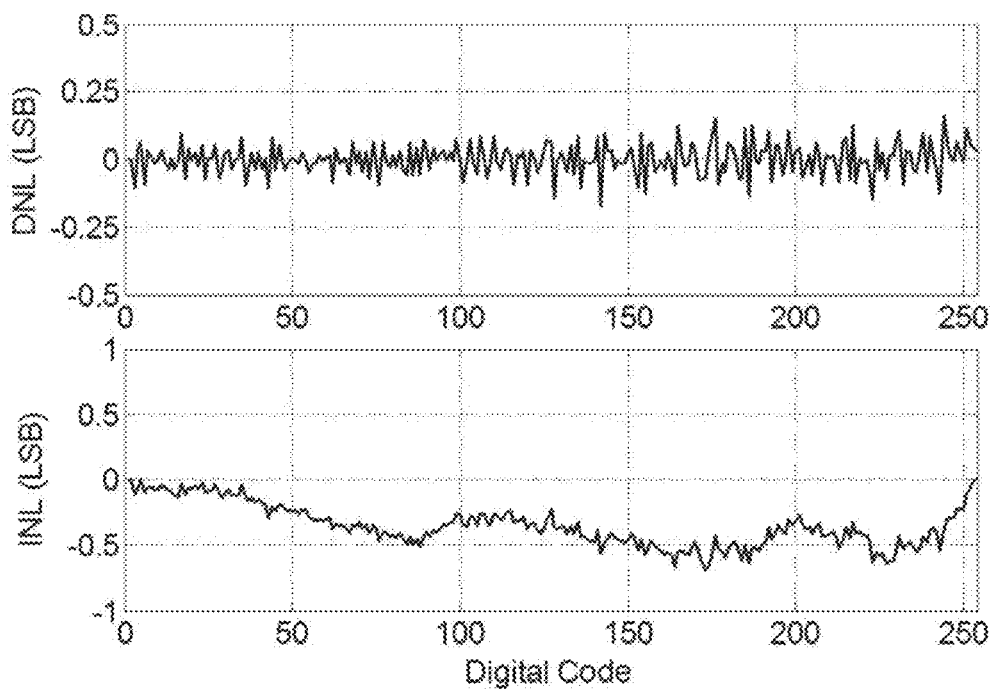

According to an embodiment of the present disclosure, by using a programmable integration time for the ADC, large range (e.g. over 80 dB (20 pA-500 nA)) of sensor current can be measured. An on-chip oscillator can provide the clock reference for the ADC. FIGS. 18A and 18B summarize the performance of the dual-slope 8 bit ADC (excluding sign bit) designed for the prototype system. As depicted in these figures, an effective number of bits (ENOB) of 7.3 bit at 4 KHz sampling rate is achieved with less than 0.6 least significant bit (LSB) integral non-linearity (INL). Such acquisition performance according to the presented exemplary embodiment of the present disclosure demonstrates that such low power ADC can provide adequate system performance for most types of implants. The person skilled in the art readily appreciates an increased performance provided by the ultra-low power, flexible, on-the-fly programmable acquisition system which can be used to calibrate the implantable device at run time (e.g. via programmable integration time) as these are desirable features for such implantable devices.

Figure 21:
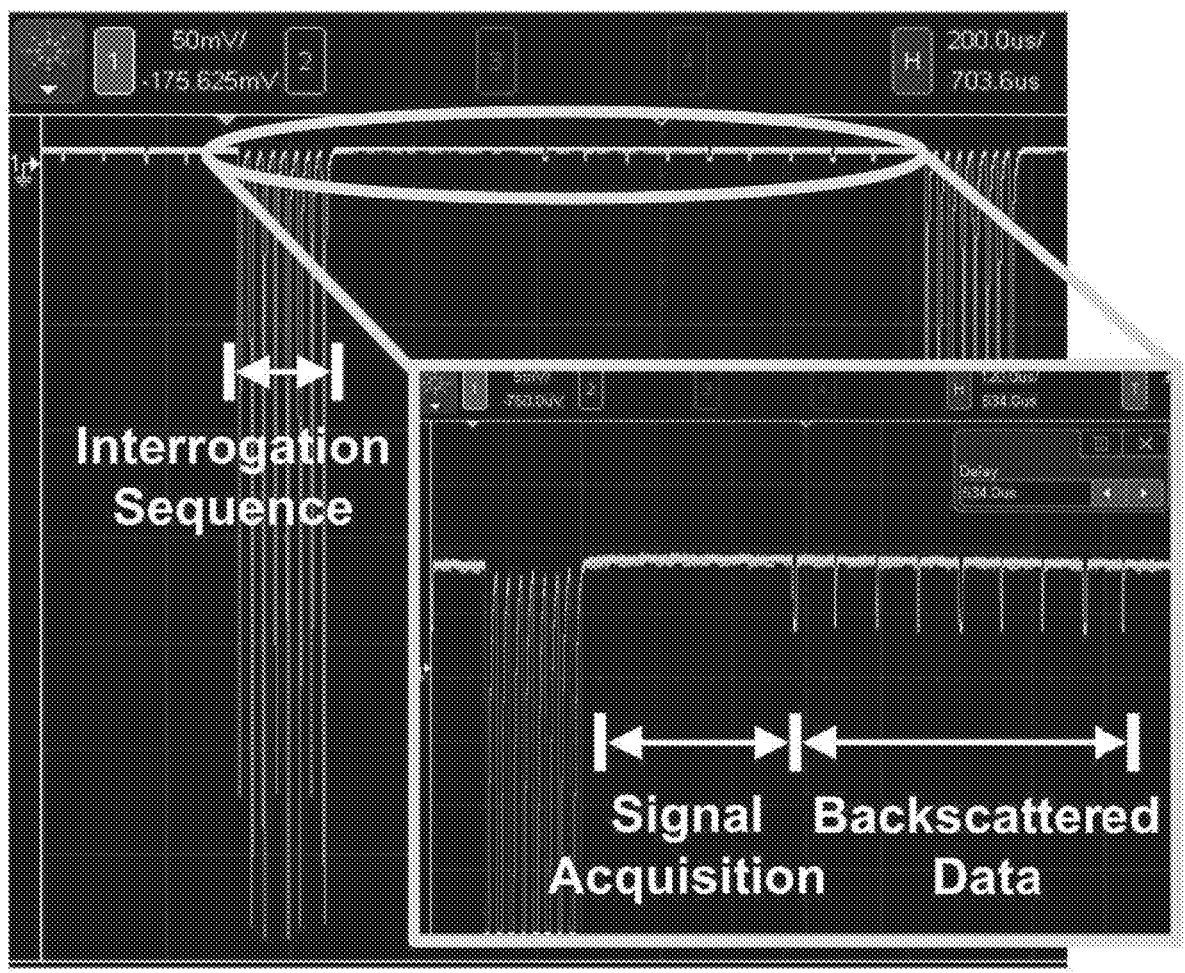
FIG. 21 shows an oscilloscope image representative of various communication sequences between the external transmitter/reader device and the integrated implantable device.

Communication to the exemplary wireless device can be provided via electromagnetic links, which can provide both power and data on the same link. An interrogation signal from an external transmitter/reader device (e.g. reader) can be transmitted to the implant using different modulation schemes. According to one exemplary embodiment, pulse-width modulation of the actual power signal can be used to convey communication data, including the interrogation signal. This allows using the same link for both power and communication. For example, ones and zeros can be coded using different pulse widths. In the exemplary prototype system, ones and zeros are coded using 2 µs and 5 µs pulses respectively. During the reader to implant communication, an implant-specific tag (e.g. address) can be sent to the sensor to wake up the sensor readout circuitry, as more than one implant can be implanted at a vicinity of one another. Such tag can initiate a data acquisition cycle of a signal detected by the specific sensor. After the sensor readout is done via the acquisition system, the output of the ADC can be serialized and transmitted wirelessly to the reader through a low-power modulation scheme. Such low-power modulation scheme provides a high enough signal to noise ratio at the reader's detecting coil. In an exemplary embodiment according to the present disclosure, data can be sent from the sensor device to the reader via pulse-width modulation of an impedance seen by the detecting coil (e.g. at the reader device) through a switch. This low-power modulation method effectively uses load-shift keying (LSK) modulation scheme in which a change in the impedance of the coil of the sensor device (e.g. via a switch, as depicted in FIG. 13) is reflected onto the reader's coil as a varying impedance and therefore a transmitted RF signal by the reader device can be affected (e.g. via backscattering) accordingly. Applicants of the present disclosure have used such low-power modulation scheme in the presented prototype system to send data to the reader at a rate up to 200 Kb/s. After each cycle of interrogation, the reader can remain silent until data from the sensor is received. Corresponding communication signal flow is shown in FIG. 21 which is described in later sections of the present disclosure.

Figure 19:
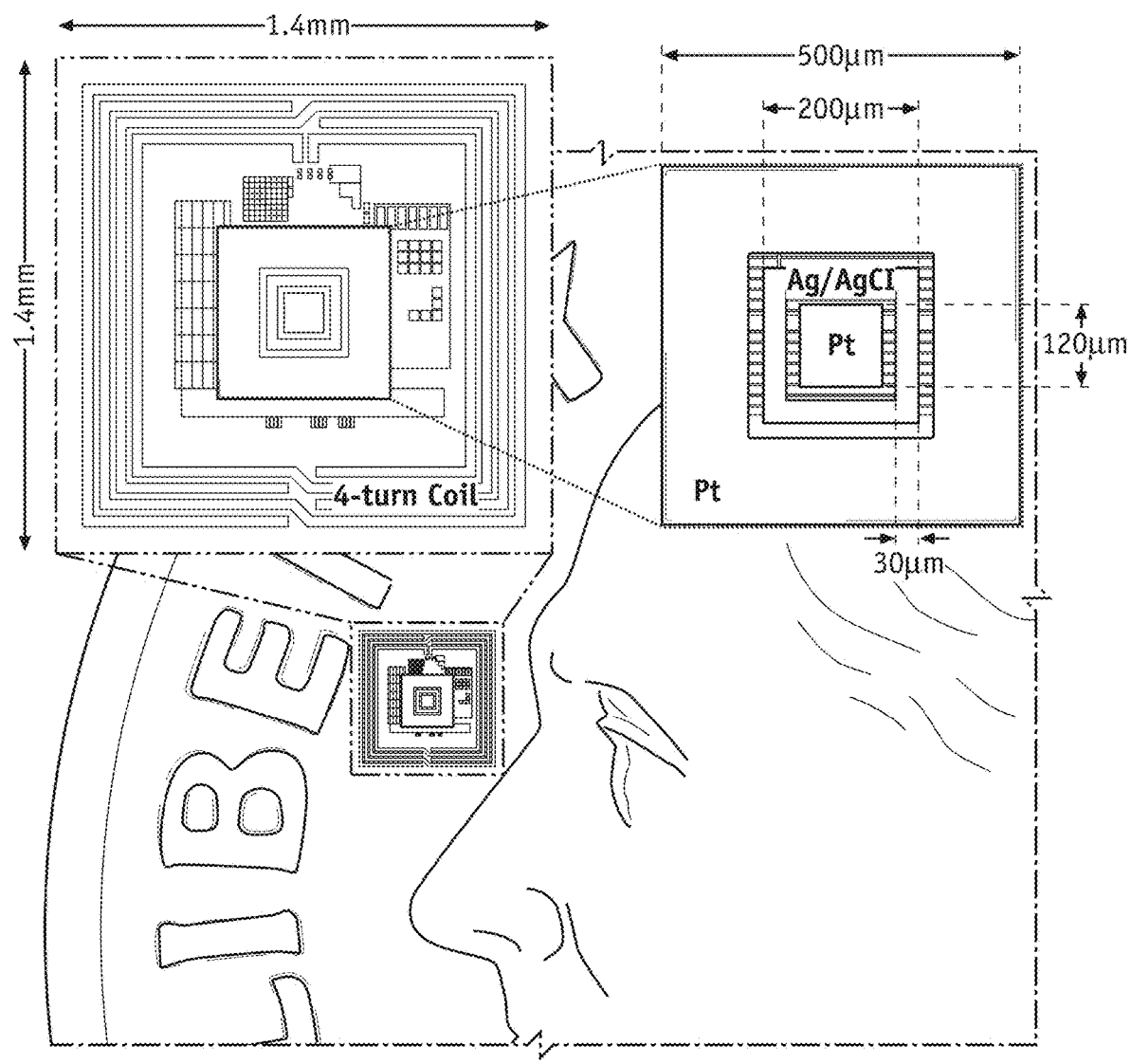
FIG. 19 shows a size of an exemplary implementation of the integrated implantable device.

With further reference to the fabrication methods according to the present disclosure provided in previous sections, a post-processing step is performed to fabricate an integrated electrochemical sensor device on the same chip (e.g. and surface) where the various electronic systems (e.g. per prototype system) are fabricated, which can also eliminate the need of complex bonding techniques associated with adding a sensor to such device. The post-processing can include lithographic deposition of thin layer (e.g. 100 nm) of Pt on working and counter electrodes and another thin layer of either Pt or Ag (e.g. 200 nm of Ag) on the reference electrode. If Ag is used for the reference electrode, plasma chlorination can be done to create a top AgCl layer to result in Ag/AgCl reference electrode using aforementioned methods which do not harm the underlying electronics. The sensor of the prototype device was functionalized in situ with Glucose Oxidase enzyme using Bovine Serum Albumin (BSA) hydrogel as the immobilization matrix and Glutaraldehyde as the crosslinking agent. Post-processing can further include covering the rest of the system (e.g. all except the electrodes) with a hermetically tight biocompatible material so as to immune the operation of the electromagnetic link of the integrated implant from effects due to operation in fluidic media as well as reduce toxicity issues in the body due to the implanted device. FIG. 19 shows the prototype system fabricated according to the various teachings of the present disclosure whose size is contrasted to a US quarter coin (e.g. 25 US cents). A first magnified view shows the 4-turn coil (e.g. shaped like a plurality (e.g. 4) of concentric similar patterns) covering a perimeter region on the top side of the integrated device with the sensor in the center of the device, and a second magnified view shows the three electrodes of the sensor, the reference electrode having an Ag/AgCl top layer. It should be noted that although a thickness of the prototype system is not shown in FIG. 19, as noted in prior sections of the present disclosure, such thickness can be down to 100 µm and not larger than 500 µm (e.g. 0.5 mm).

Figure 20:
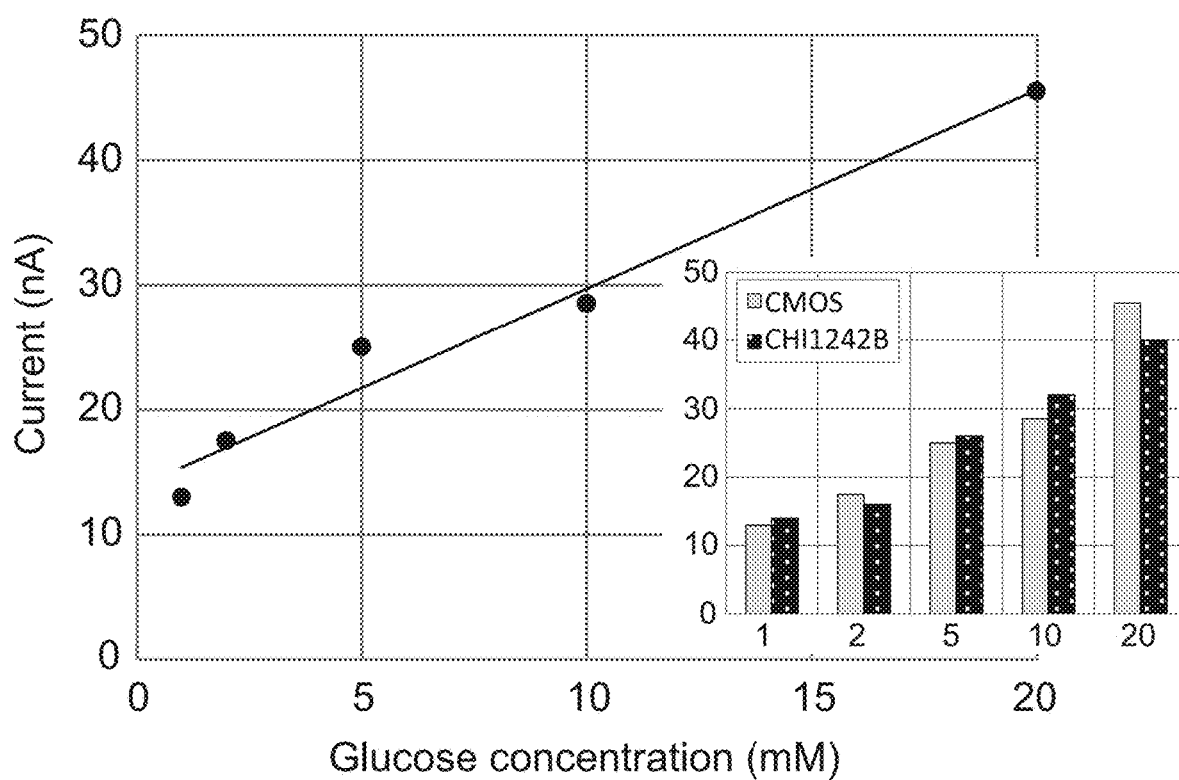
FIG. 20 shows a graph representative of a performance of the exemplary implementation for detecting glucose concentration and contrasted to a performance of a commercial potentiostat.

The functionality of the implanted prototype sensor was validated in glucose measurement over 0-20 mM concentration using amperometry with 0.4V potential between the working and reference electrodes. FIG. 20 shows the result (e.g. labeled CMOS) along with the reading from a commercial potentiostat (CHI1242B).

Power to the implanted device can be provided via an external device (e.g. reader device). Configuration of such external device can vary based upon requirements and applications. Functionality of such device can be provided by an application specific IC or a system with discrete components. As an example, an external printed circuit board (PCB) with an LC resonator is used as proof of concept. The resonator is tuned to the same frequency as the implant resonator thus transferring power efficiently to it. Using the prototype system in combination with the external PCB, 22 dBm of power was transmitted by using a 2×2 cm² external inductor coil on the external PCB, which was separated from the CGM implant by 5 mm of muscle tissue and 5 mm of air. The link performance was insensitive for up to ±3 mm center-to-center misalignment between the reader and the implant (e.g. center of corresponding coils).

External Transmitter/Reader

The external device acts as a transmitter and a reader and can consist of some commercial components to generate radio frequency signals (e.g. UHF, 900 MHz ISM band, etc.) of a desired frequency and timing, and an external coil to couple to the integrated sensor device. It is noted that according to some embodiments of the present disclosure, a handheld device, such as, for example, a cellular phone, fitted with special software can be used as the transmitter/reader.

According to some embodiments of the present disclosure, the external device can comprise an array of coils (e.g. more than one) that are arranged in a particular pattern. Same electronics can be used to sequentially power each coil and measure a received signal to determine the position of the sensor based, for example, on a power of the received signal. The coil or set of coils with a higher received signal power can be used for effectively powering and communicating with the integrated device as described in the previous sections of the present disclosure. Such detection algorithm and selection of coils to communicate and power the integrated device provides a higher energy density from the coil(s) and allows achieving good power transfer efficiency to the chip while being able to withstand small changes in implant position with time. The array of coils and corresponding arrangement pattern can be further used to shape a resultant electro-magnetic (EM) field in order to focus on the implant location, increasing power efficiency and possible implant depth.

According to other embodiments of the present disclosure, the reader and transmitter functions of the external device can be incorporated in non-dedicated devices, such as personal devices like cell phones, tablets and the like. This can be done by designing the integrated sensor system around frequencies which such non-dedicated devices can operate upon, and incorporating the reader and transmitter functions (e.g. modulation, demodulation, RF power transmit etc.) in a chipset of the non-dedicated device.

FIG. 21 shows communication signals detected between the reader and the implant which are shaped as pulses of varying length. Actual signal at the antennae (e.g. RF at 900 MHz ISM frequency band) is modulated by these pulses. Once the interrogation signal sent during an interrogation sequence is received by the sensor, glucose reading starts within a signal acquisition sequence and the result of the acquisition is transmitted to the reader during a backscattered data sequence in which data representing the acquired data is provided the to the reader via modulation of the impedance of the coil of the integrated sensor. The table depicted in FIG. 22 summarizes the performance of the prototype system and compares it to state-of-the-art systems as described in references [1, 2], both incorporated herein by reference in their entirety. The prototype system, fabricated using the various embodiments according to the present disclosure, is the smallest reported wireless CGM system with more than 15 times reduction in area and 60 times reduction in volume while providing comparable performance to the current state-of-the-art systems. The person skilled in the art readily appreciates the advantages provided by such integrated device and underlying fabrication methods, which allow for a small size (e.g. 1 mm×1 mm×(100 µm–500 µm)) and low power consumption device while still providing adequate performance for one of the most complex sensing scenario of measuring glucose.

Implantation and Removal Methods

The integrated sensing device according to the various embodiments of the present disclosure can be implanted in the skin, subcutaneous tissue, intraperitoneal cavity, organs, brain, muscle, or in other tissues. An incision can be made in the body for implantation. Alternatively, an appropriate gauge trocar and/or needle can be used for implantation of the device. The person skilled in the art readily appreciates the implantation flexibility provided by the small size of the implantable device according to the various embodiments of the present disclosure, such as usage of a trocar and/or needle of an appropriate gauge to completely embed the implantable device in the tissue. Removal of such implant can be performed, for example, via a simple incision, or by using a trocar followed by a grabbing instrument.

Actuation

According to a further embodiment of the present disclosure, the integrated electrochemical sensor according to the teachings of the present disclosure can be used for actuation as well. The electrodes of the sensor can be used to flow current through a corresponding local environment .by forcing a voltage or current across the electrodes. For small sensors which have limited output current capacity, this can be done in pulsed mode so as to be able to deliver enough current to the local environment. A small sensor can have a capacity to provide current which is smaller compared to the one required by the tissue region intended for actuation. For example, continuous actuation of heart muscle with less than a microampere of current available for a wireless integrated sensor according to the present teachings can be difficult. However, the wireless integrated device can be operated in a pulsed mode to overcome such low current limitation. This can be done by utilizing energy storing elements (e.g. capacitors) within the wireless integrated device to accumulate electrical energy for actuation. Although larger surface area of the electrodes can help increase the current range of the electrochemical system, the overall current (e.g. in continuous operation) is still limited by the wireless power transfer to the system. Multiple such devices can be used in synchronization to improve actuation. The advantage of small size and small current (or voltage) is that very local actuation is possible.

Figure 23:
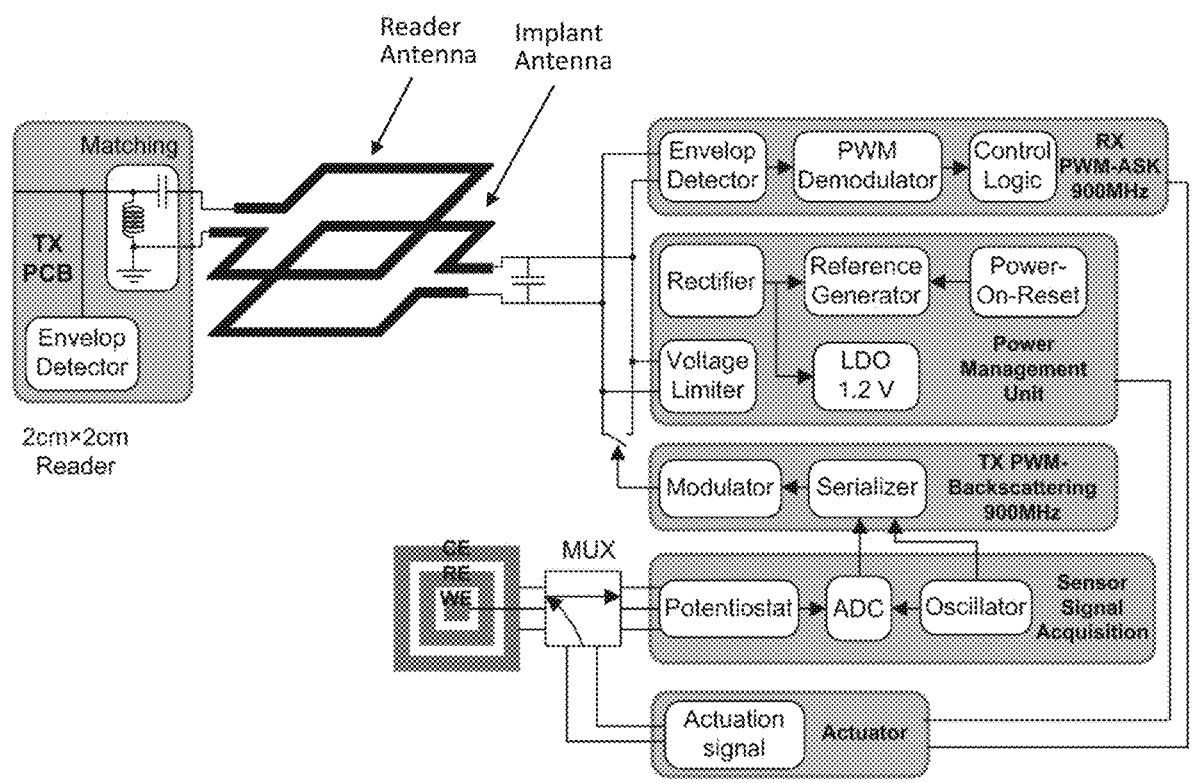
FIG. 23 depicts the block diagram of the system depicted in FIG. 13 with an added actuator unit which allows the system to perform an actuating task.

Actuation can be activated by a control logic signal upon receiving a specific tag sequence that tells the integrated implantable device to begin actuation along with the relevant parameters (e.g. duration, actuation waveform etc.). Such integrated implantable device configured to perform actuation is depicted in the block diagram of FIG. 23. An actuator unit (e.g. Actuator of FIG. 23) allows performing the task of actuation by injecting current to electrodes (e.g. CE, RE, WE) of the sensor. A switch (e.g. MUX) can allow connection of the electrodes to either the sensor signal acquisition unit for sensing, or to the actuator unit for actuation. Upon receipt of the actuating tag sequence from an external device, a capacitor bank (e.g. uses as an energy storing subsystem), which can reside within the actuator unit, can be charged through the wireless power link. Also, a control logic based on the tag sequence can connect the electrodes (e.g. working and counter via the switch MUX) to the actuator unit of the implantable integrated device. A waveform shaping circuit of the actuator unit can convert the electrical energy of the capacitor bank to a desired waveform (e.g. voltage, current) signal through the waveform shaping circuit. This waveform signal is then fed to the electrodes which transfer a corresponding energy to nearby tissue (e.g.

where device is implanted) for actuation purposes. A waveform signal can be obtained by simply connecting the electrodes directly to the capacitor bank (e.g. via switch MUX) which causes the capacitor bank to discharge exponentially based upon the tissue conductance (e.g. and capacitance value of the bank). Other options for waveform generation can be current limiting circuits which allow a constant current for the entire actuation period. A multiplexer (e.g. switch) can be used to make sure that both the sensor and the actuator circuits are not connected to the electrodes at the same time. The person skilled in the art readily appreciates the flexibility provided by exemplary embodiment according to teachings of the present disclosure as depicted in FIG. 23 for using the integrated electrochemical device in both a sensing and an actuating mode. The actuation can be used for many purposes including, but not limited to, cleaning the electrode surfaces, cleaning the sensor surface, therapeutic actuation of nerves or other tissues (e.g. heart tissue). Multiple of the devices with controlled actuation can allow very controlled (e.g. focused) local actuation, owing to the small size of the device.

Exemplary Case 2: Fully Wireless Implantable Drug Delivery Device

Based on the above description of a wireless implantable sensing device, a wireless implantable drug delivery device according to a further exemplary embodiment of the present disclosure is now presented. The function of drug delivery can be either added to or exchanged with the sensing function of the wireless implantable sensing device discussed above. According to some embodiments of the present disclosure, such remote controlled wireless device can be implanted as a hermetically sealed system in order to avoid tissue response problems, and can be remotely actuated by using a very specific high-frequency signal (tag) transmitted by the external reader.

Miniaturization of the overall size and power consumption of the wireless implantable drug delivery device according to the present disclosure allows controlling the precise location of the drug delivery, targeting specific localized areas within a body. As a result, a reduction of the overall quantity of dispensed chemistries is possible, which can therefore avoid many of the toxic side-effects often found when potent medications are injected without much control.

The implantable drug delivery device according to the present disclosure can be used to address the specific problem of treatment of brain tumors through chemotherapy. As the blood-brain barrier often prevents the use of chemotherapy for treatment of brain tumors, the remote control feature over time and location of treatment provided by the implantable drug delivery device according to the present disclosure can be a useful tool serving a critical and presently unmet medical need. When coupled with the sensing feature described in the above Exemplary Case 1, on-chip measurements can further trigger/control the delivery of medications by the implantable drug delivery device.

Figure 24:
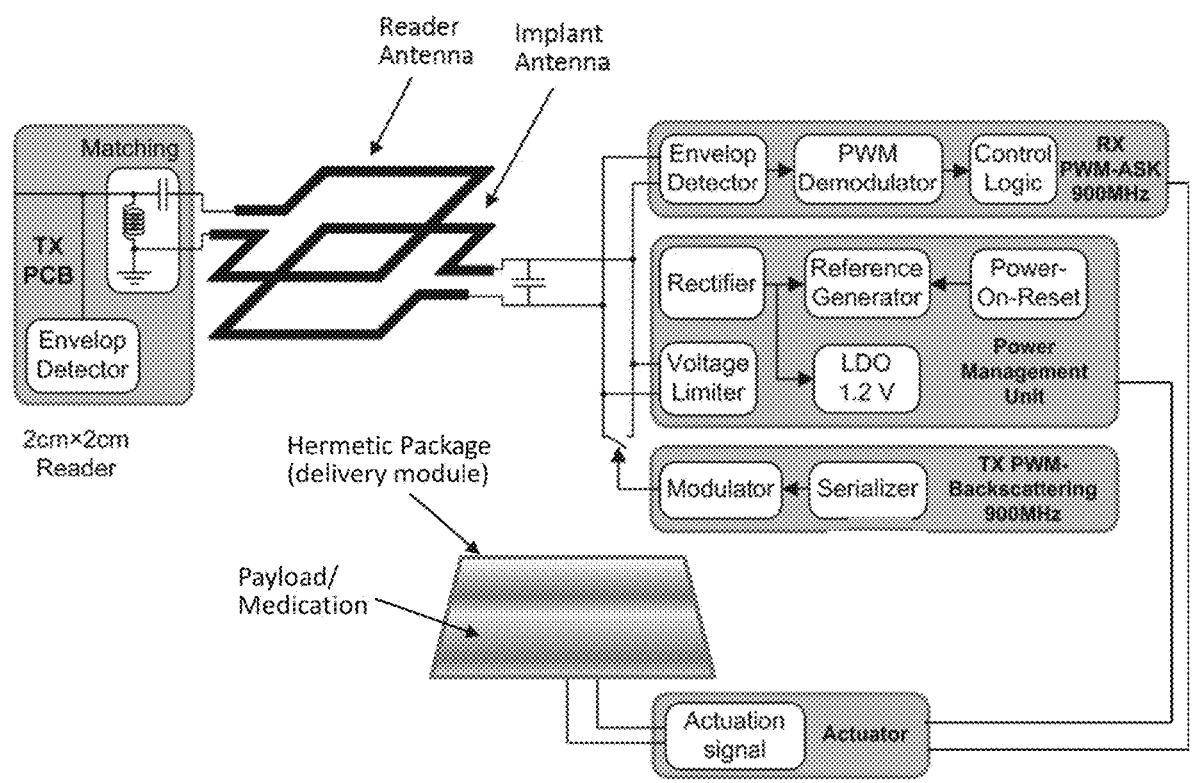
FIG. 24 depicts a block diagram of a system comprising a wireless implantable integrated device, a corresponding external transmitter/reader and an interface region between the two, where the implantable integrated device comprises an actuator for dispensing a payload of a delivery module.

In the following sections a wireless implantable drug delivery device according to the present disclosure is discussed, which can be further fitted with sensors. The electronic components of such system, as depicted in FIG. 24, are similar to the electronic components depicted in the system of FIGS. 13 and 23, and include a wireless communication interface (labeled RX PWM-ASK 900 MHz), a wireless power delivery system (labeled Power Management Unit), and an actuation system (labeled Actuator) to open the hermetic package that contains a medication to be delivered (labeled Payload/Medication). To avoid deleterious side-effects when these electronic components interact with the surrounding tissue and/or the medication to be delivered, such components are encapsulated in an encapsulation chemistry (not shown). Similar electronic components of FIG. 24 to ones of FIGS. 13 and 23 have similar functionalities as described with reference to latter figures.

Figure 25:
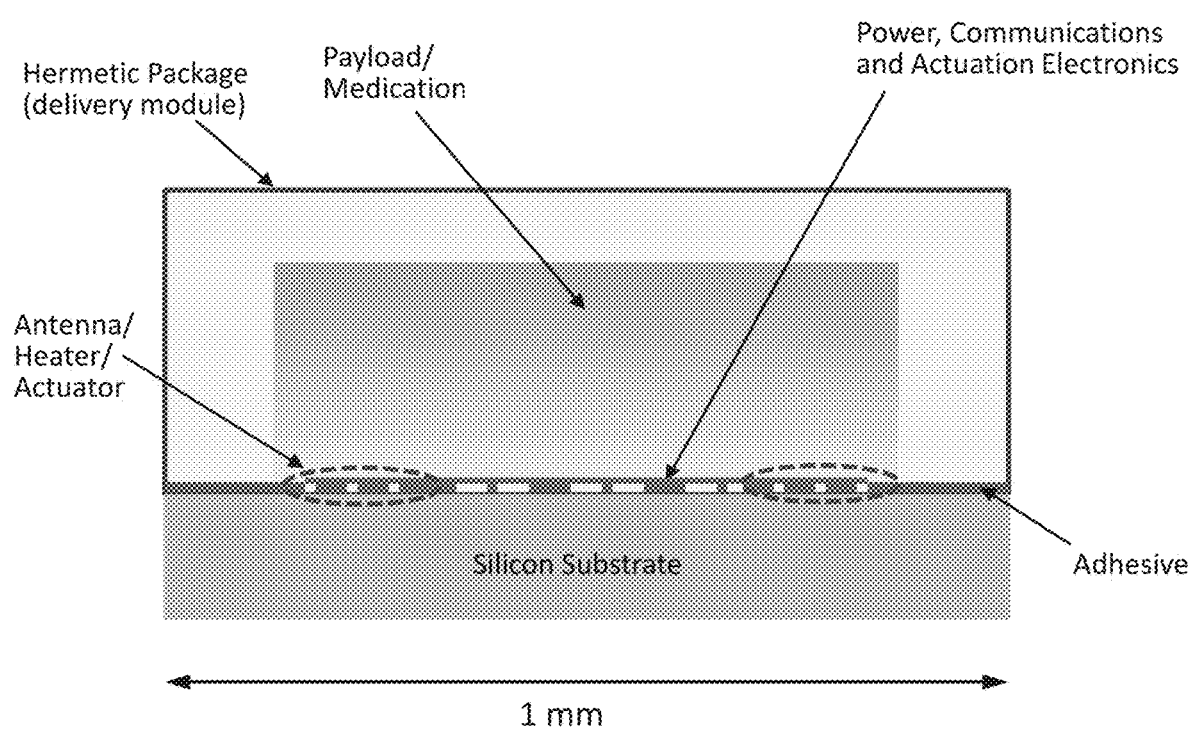
FIG. 25 shows a simplified cross section of the wireless implantable integrated device of FIG. 24.

FIG. 25 shows a simplified cross section of the wireless implantable drug delivery device according to the present disclosure. As can be seen in FIG. 25, the implantable device comprises a silicon substrate upon which the electronics components discussed with respect to FIG. 24 are fabricated. The silicon substrate further serves as a base to the hermetic package that contains the medication. Adhesive strips are further used to fixate the hermetic package upon the silicon substrate. A large side of the wireless implantable drug delivery device shown in FIG. 25 has a size of 1 mm or less.

With reference to FIG. 25, the hermetic package of the wireless implantable drug delivery device of the present disclosure can be made in many materials as well as geometries. Some such materials can be injection molded polymers, micro-machined silicon, artificial foams or bubbles, hollow microbeads and even "smart" composites, all known to a person skilled in the art.

According to an exemplary embodiment of the present disclosure, the hermetic package (delivery module) can be made to contain 1 microliter of chemistry (medication), which therefore provides a bottom limit of the delivery module size on the order of 1×1×1 mm. A person skilled in the art knows of manufacturing techniques that can provide non-cubic delivery geometries, which can therefore allow various shapes for the delivery module. According to some exemplary embodiments of the present disclosure, the delivery module shape is an asymmetric "can" or a fully symmetric sphere. According to further exemplary embodiments, several such delivery modules, either of a same size or of different sizes, are provided in the wireless implantable drug delivery according to the present disclosure so as to allow delivery of different dosages at different times. Such delivery modules can be activated via different actuators and therefore used at different times.

One challenge of drug delivery is the problem of filling the delivery module with reagent (e.g. medication) and subsequently sealing the module without compromising the chemical potency of the reagent. Conventional sealing techniques known to a person skilled in the art, such as heat treatment to cure glues or to harden epoxies, may deteriorate the reagent (medication), especially if delicate biomolecules are to be delivered. Moreover, if the reagent is in liquid form, it is impossible to use most vacuum sealing technologies. Even the development of methods for filling medication into the small desired geometries (of the delivery module) within a reasonable timeframe can be very challenging.

Alternatively, and in order to overcome the above shortcomings of the conventional sealing techniques, sealing of the delivery module according to the present disclosure can be provided by thermal setting of glues through local heating of the seal, UV-setting polymer based adhesives that can be hardened by irradiating ultraviolet light onto these polymers, or room-temperature setting glues. In such situations, MEMS type technology can provide small valves to be able to fill a pre-sealed delivery module through the small valves. FIG. 25 shows an adhesive which can provide the sealing of the delivery module.

Quality of the seal used for sealing of the delivery module according to the present disclosure can be remotely affected (controlled) by either heating or applying pressure onto the seal. On previous occasions, microfluidic devices have been constructed with paraffin or other low-temperature materials that were heated through local resistive heating with a circuit that delivers a short pulse of high current or a pulse of laser light. This heat pulse is applied to melt the paraffin and provide a leak for the medication in the package to diffuse into the surrounding tissue. When translating this concept into wireless implantable devices that must function in-vivo, care must be taken to shrink the sizes of the heaters to reduce the overall power consumption of the device while eliminating any possible overheating of the surrounding tissue.

According to an embodiment of the present disclosure, a same structure of the wireless implantable drug delivery device is used to provide the functionalities of (a) a heater, (b) an antenna and (c) an actuation resistor. For these purposes, the heater can be constructed as a coil on the outside of an electronics chip as shown, for example, in FIG. 19 (4-turn coil), where the chip, positioned in the inside of the coil, comprises the electronic components discussed above with respect to FIG. 24. Based on the relative positioning of the coil and the chip, the coil can provide local heating of the rim of the chip. This is shown in FIG. 25 where the antenna/heater/actuator is positioned in an outside area of the power/communication/actuation electronics (chip) at the vicinity of the adhesive which seals the delivery module.

With further reference to the sealing provided by the adhesive as shown in FIG. 25, in order to generate a high enough current pulse for significant heating of the antenna/heater/actuator, it may be necessary to define a large capacitor on-chip that can be charged slowly over time and discharges through the resistive heating geometry of the coil that forms the antenna/heater/actuator. The coil can be designed to maximize both resistive and eddy current losses to maximize heating and minimize the required power.

According to a further embodiment of the present disclosure, thermal actuation to affect the sealing of the delivery module is provided by a shape memory material, in which temperature pulses induce a phase transformation in the memory material, and consequently high pressure which can rupture the seal.

Figure 26:
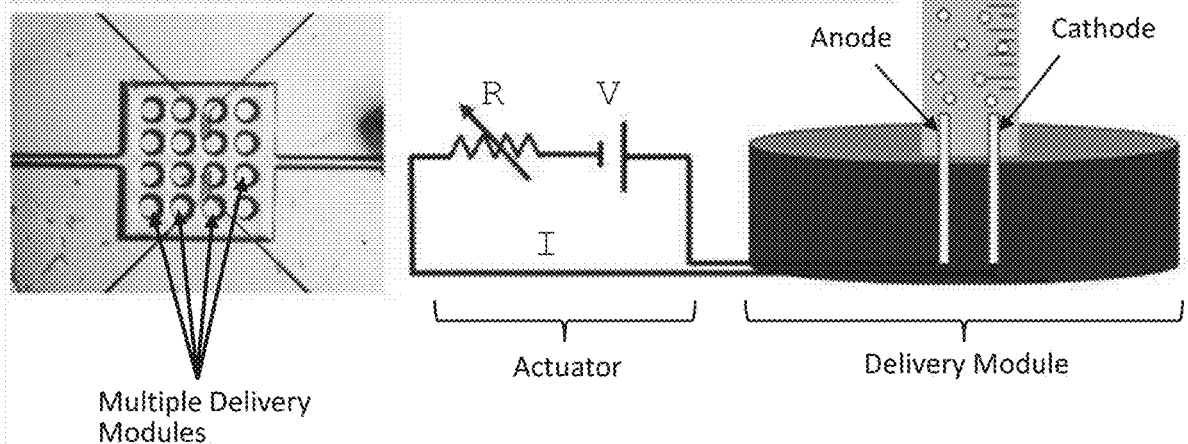
FIG. 26 shows an exemplary actuator, payload and delivery module of the wireless implantable integrated device of FIG. 25, represented by an electrochemical cell that facilitates a dissociation reaction of water into its constituent elements.

According to some embodiments of the present disclosure, the pressure used to rupture the sealing of the delivery module can be generated by gas obtained through an electrochemical reaction, as shown in FIG. 26. In particular, as known to person skilled in the art, the electrochemical dissociation of water from $H_2O$ into its constituents, released as gaseous hydrogen and oxygen, requires 0.83+1.23=2.06 Volts to occur, as governed by the following reactions and associated energy:

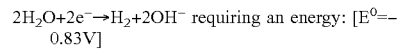

$2H_2O+2e^- \rightarrow H_2+2OH^-$ requiring an energy: $[E^0=-0.83V]$

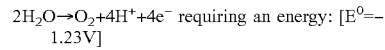

$2H_2O \rightarrow O_2+4H^++4e^-$ requiring an energy: $[E^0=-1.23V]$ where the number of molecules that are dissociated depends on the applied current according to Faraday's laws, and each dissociation event produces one molecule of hydrogen and one half of an oxygen molecule.

With reference to FIG. 26, a person skilled in the art can recognize an electrochemical cell that facilitates the dissociation of water into its constituent elements per the above electrochemical reactions. Hydrogen is generated at the cathode and oxygen is released at the anode. In large volumes, this electrochemical process produces only small amounts of gas and insignificant pressure changes, but in confined microgeometries such as the delivery module used in the wireless implantable drug delivery device of the present disclosure, hydrogen evolution can lead to very rapid pressure changes of up to 3 atmospheres per second pressure increase.

With further reference to the electrochemical dissociation reaction depicted in FIG. 26, efficiency of the dissociation reaction can be increased by using a solution (electrolyte) between the electrodes with reasonably low resistance which can therefore promote increased conduction. In the case of the wireless implantable drug delivery device, increased conduction of the encapsulated chemistry (drug+electrolyte) can be obtained by using a liquid form of the chemistry with presence of salt or other ions in the chemistry so as to promote conduction. In some cases, the drug to be delivered may be able to be mixed in an electrolyte solution without losing its efficiency, hence simplifying system design. This also allows using other dissociation reactions at lower potentials to create other gases (e.g. chlorine) to create internal pressures which can rupture the sealing of the delivery module. The small quantity of gases generated by such electrochemical reaction can be within the safety and irritation limits and not harmful to tissue surrounding the implantable delivery device.

Figure 27A:
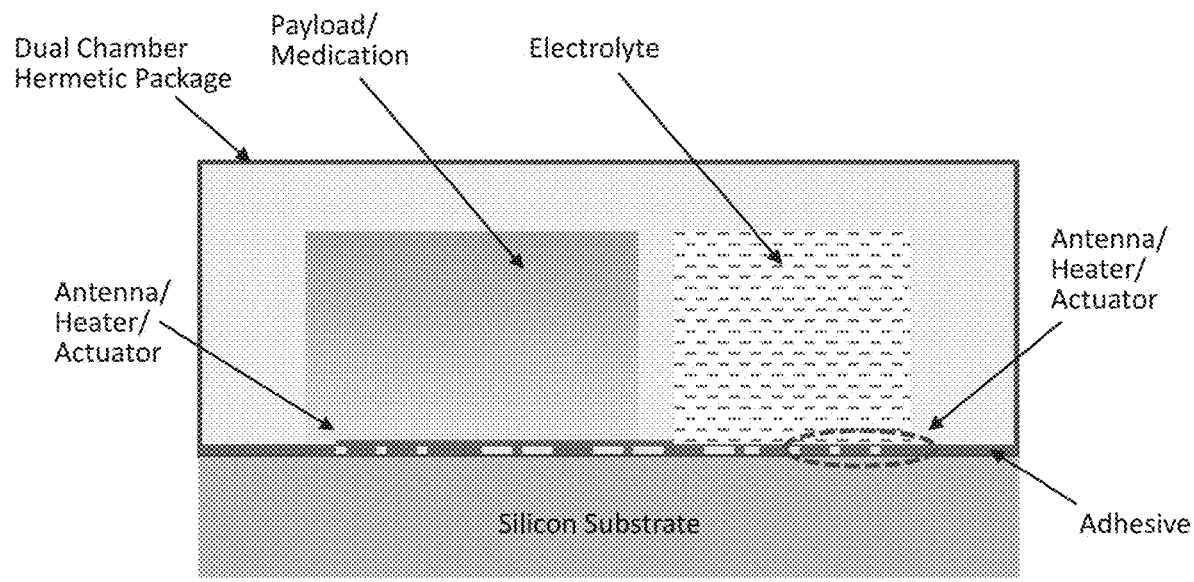
FIG. 27A and FIG. 27B show a two-chamber configuration of the delivery module, where an electrochemical reaction can take place in a chamber next to the chamber containing the payload (drug to be delivered).
Figure 27B:
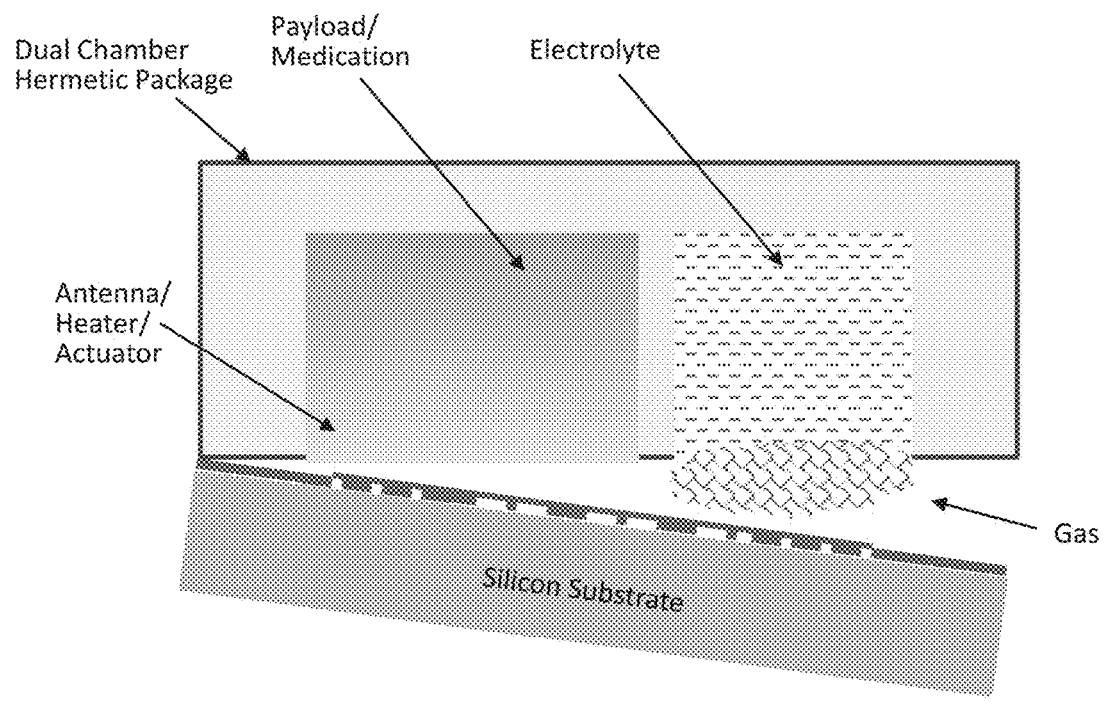

The encapsulated chemistry needs to be appropriately designed to be robust with respect to the electrochemical requirements of the actuation mechanism. In other words, the mixture of the electrolyte and the drug to be delivered needs to produce enough pressure to cause rupture of the seal while using the smallest amount of electrolyte so as to keep the efficiency of the drug to be delivered. This is not always feasible. It follows that according to further embodiments of the present disclosure a two-chamber configuration is used for the wireless implantable drug delivery device, where the electrolyte used for the electrochemical reaction and the drug to be delivered are contained in separate chambers. In such a two-chamber system, the electrochemical reaction can take place in a chamber next to the chamber containing the payload (drug to be delivered), with the sole purpose of rupturing the seal to allow dispensing of the payload as shown in FIGS. 27A and 27B.

Power generation for wireless implants often limits the minimum size of such devices. Batteries can be deployed to power such devices, but these are bulky, must be eventually replaced and often lead to toxicity concerns. Supercapacitors offer a short-term alternative but must be charged with some method. If battery power is to be avoided, two possible power generation methods for implants are 1) photovoltaic on-chip power generation along with infrared (remote) laser power from the reader, as described, for example, in the above referenced US Patent Publication No. 2014/0228660, herein incorporated by reference in its entirety, and 2) microwave inductive coupling between coils in the reader and the implant as described above in relation to FIGS. 13, 23 and 24. Remote optical powering from the reader can limit the location of the implants to within less than 5 mm from the surface of the skin, as deeper implants require dangerously high power densities irradiated through the skin, and therefore pulsed power approaches may be used for implants located farther than 5 mm from the surface of the skin. Inductive coupling can enable deeper implant depths, depending on the tissue absorption of the microwave frequencies used. For millimeter-sized devices, such as the wireless implantable drug delivery device of the present disclosure, a desired frequency is 900 MHz, which matches much of the cellphone technology and provides a depth of communication and powering of approximately 1 cm into human tissue. A major advantage of microwave powering is the ease with which it can be integrated with standard CMOS electronics, whereas the most important advantage of optical power transfer is the smaller size of the implant enabled by eliminating the need of antennas that have to approximately match the wavelength of the powering radiation.

Figure 28:
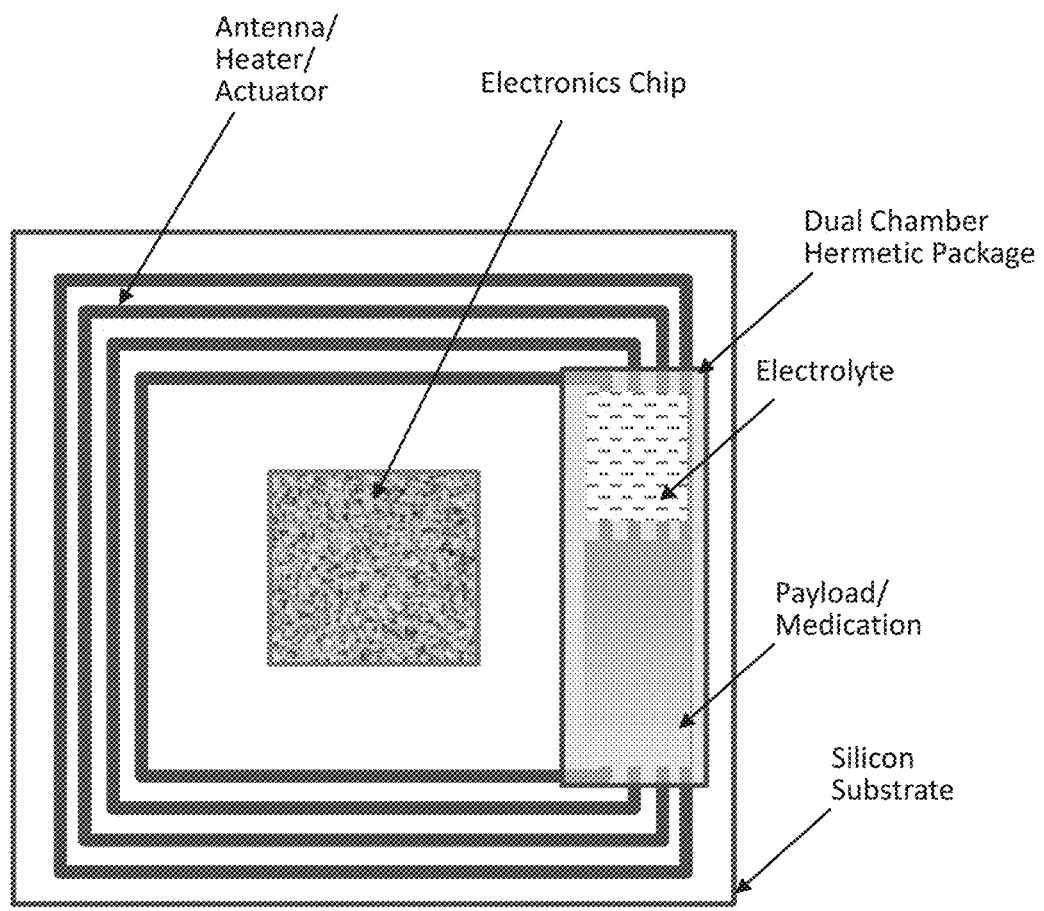
FIG. 28 shows a simplified top view of a wireless implantable drug delivery device according to an embodiment of the present disclosure comprising a dual chamber configuration.

FIG. 28 shows a simplified top view of a wireless implantable drug delivery device according to an embodiment of the present disclosure comprising elements discussed above, including a silicon substrate serving as a base to the implantable device, an electronic chip comprising circuitry to implement the various electronic components discussed with respect to FIG. 24, an antenna/heater/actuator element formed at a periphery of the implantable device serving as coils for the inductive coupling between the implantable device and a corresponding reader/controller, and a dual chamber hermetic package which contains the medication to be delivered and an electrolyte solution in separate sealed chambers. The sealed chamber containing the electrolyte along with the coil used as conductors to provide the functionality of the electrochemical cell discussed in relation to FIG. 26, can cause the above discussed electrochemical reaction to generate gases at high pressure that can rupture the seal and therefore allow the medication in the second sealed chamber to be released in surrounding tissue, as described in relation to FIGS. 27A and 27B.

Figure 29:
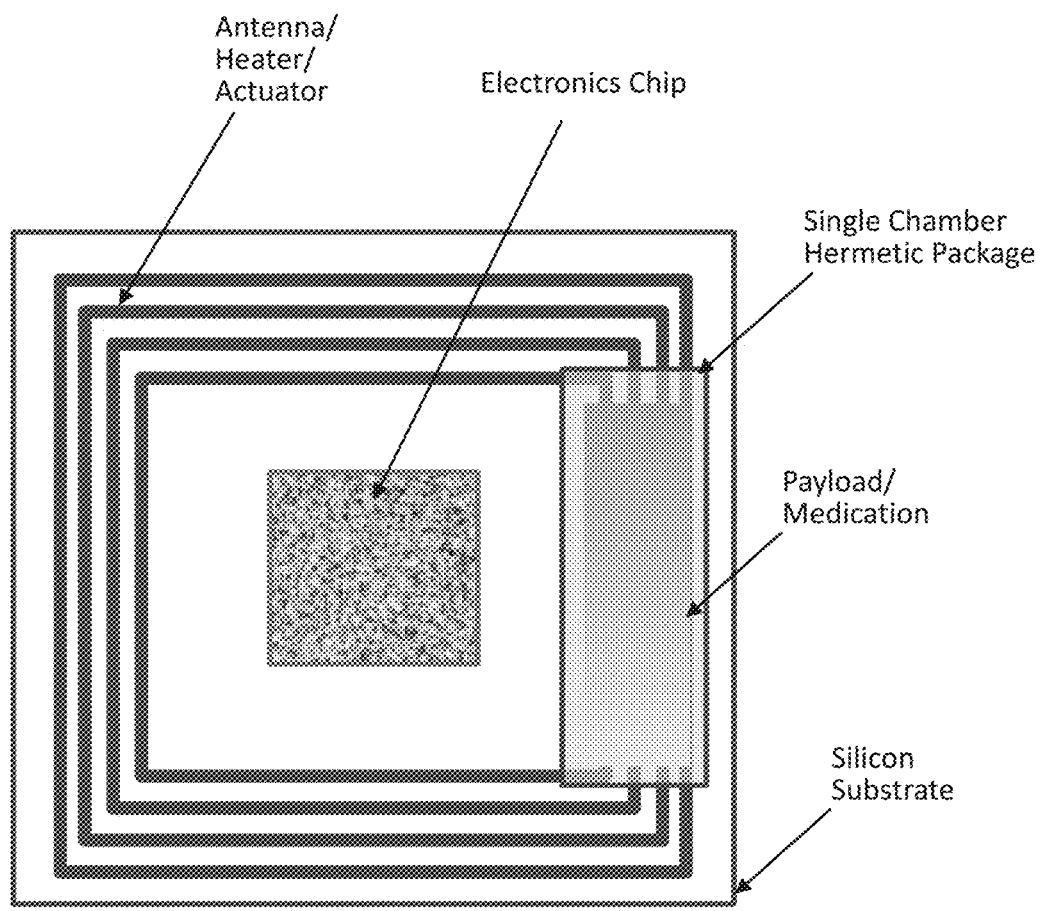
FIG. 29 shows a simplified top view of a wireless implantable drug delivery device according to an embodiment of the present disclosure comprising a single chamber configuration.

FIG. 29 shows a simplified top view wireless implantable drug delivery device according to a further embodiment of the present disclosure, where a single sealed chamber is used to contain the medication to be delivered. Rupturing of the seal to dispense the medication is performed via heating of the seal provided by the antenna/heater/actuator element as discussed above in relation to FIG. 25. Other elements of the implantable device depicted in FIG. 29 are similar to the elements discussed in FIG. 28.

With further reference to the wireless implantable drug delivery device depicted in FIGS. 28 and 29, actuation of the implantable device that triggers dispensing of the medication is only possible through electronic control via an external reader/controller (keyed/locked to the implantable device) and therefore inadvertent leaks of the payload/medication are avoided. A remote signal generated by the external reader/controller actuates the CMOS electronics chip which in turn starts an electronic process of generating enough energy to release a pulse of either heat (e.g. FIG. 29) or pressure (e.g. FIG. 28) to open leakage paths through which the payload can be dispensed. Further details of the actuation, including techniques for storage of energy for providing such pulses in a capacitor bank for later discharge, can be found in the above description as related to the actuator of FIG. 23.

The wireless implantable drug delivery device according to the present disclosure uses carefully selected materials that can withstand the corrosive in-vivo environment that the implantable device is subjected to for long time periods while reducing the effect of the implant on the surrounding tissue. These can be biocompatible materials, including and not limited to materials such as silicones, polyurethanes, poly vinyl acetate (PVA), etc. Furthermore, some possible (non-limiting) adhesives can be, for example, USP Class VI adhesives (e.g. from Masterbond). A person skilled in the art would know of other biocompatible materials to be used in the wireless implantable drug delivery device according to the present disclosure.

With further reference to the wireless implantable drug delivery device according to the present disclosure, the single/dual chamber used to carry the drug to be delivered, and optionally the electrolyte, can, as discussed above, be bonded to the silicon substrate of the implantable device. According to some embodiments of the present disclosure, the chamber can either be a self-contained silicon-on-insulator (SOI) chamber, a micro-machined fluidic chamber as provided in a fluidic system, or a filled cup whose rim can be bonded to the silicon cover surface (FIGS. 25, 27A, 27B), all of which are known to a person skilled in the art.

Figure 30:
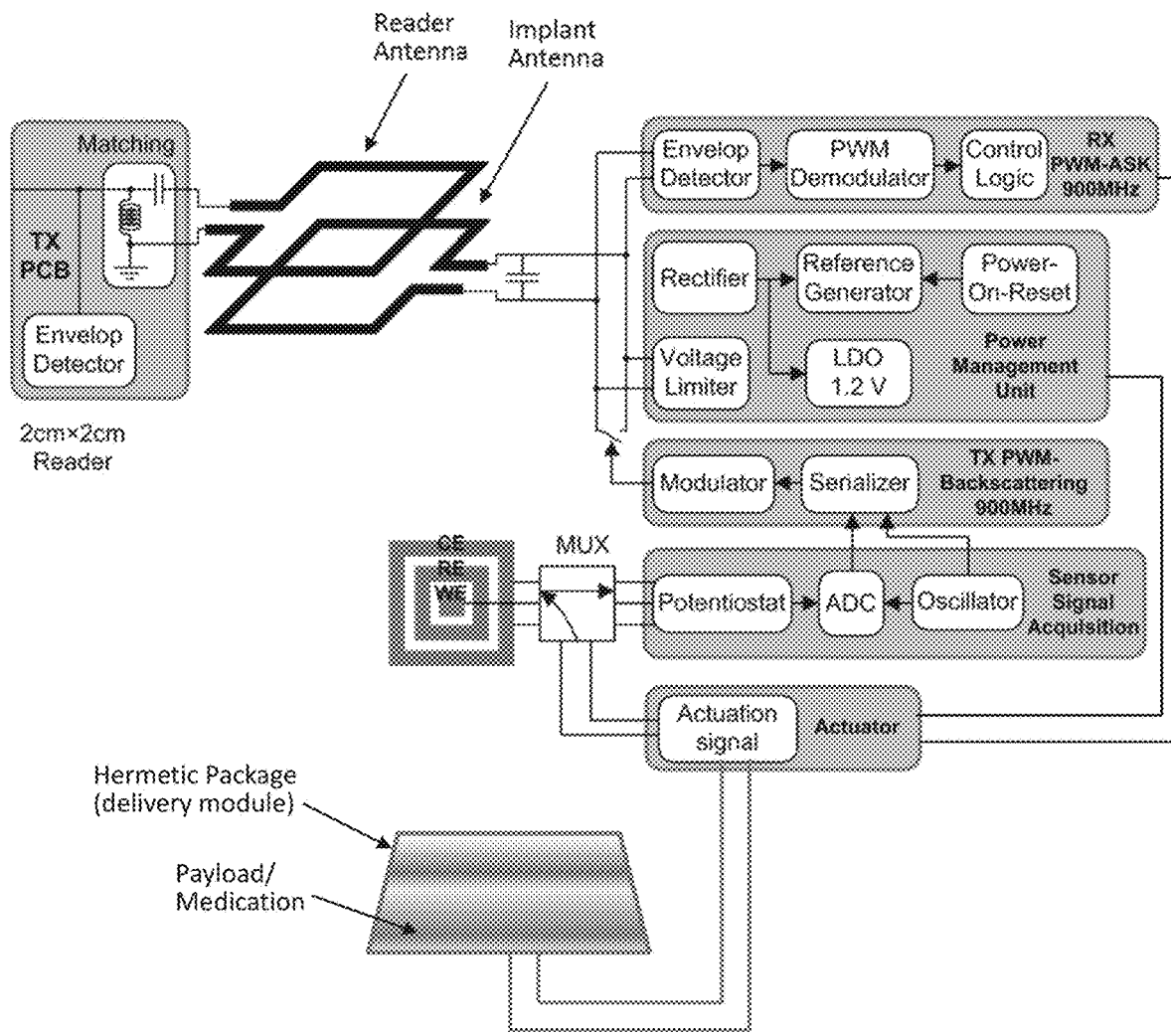
FIG. 30 depicts the block diagram of the system depicted in FIG. 29 with an added sensor/electrode unit which allows the system to perform a sensing task.
Figure 31:
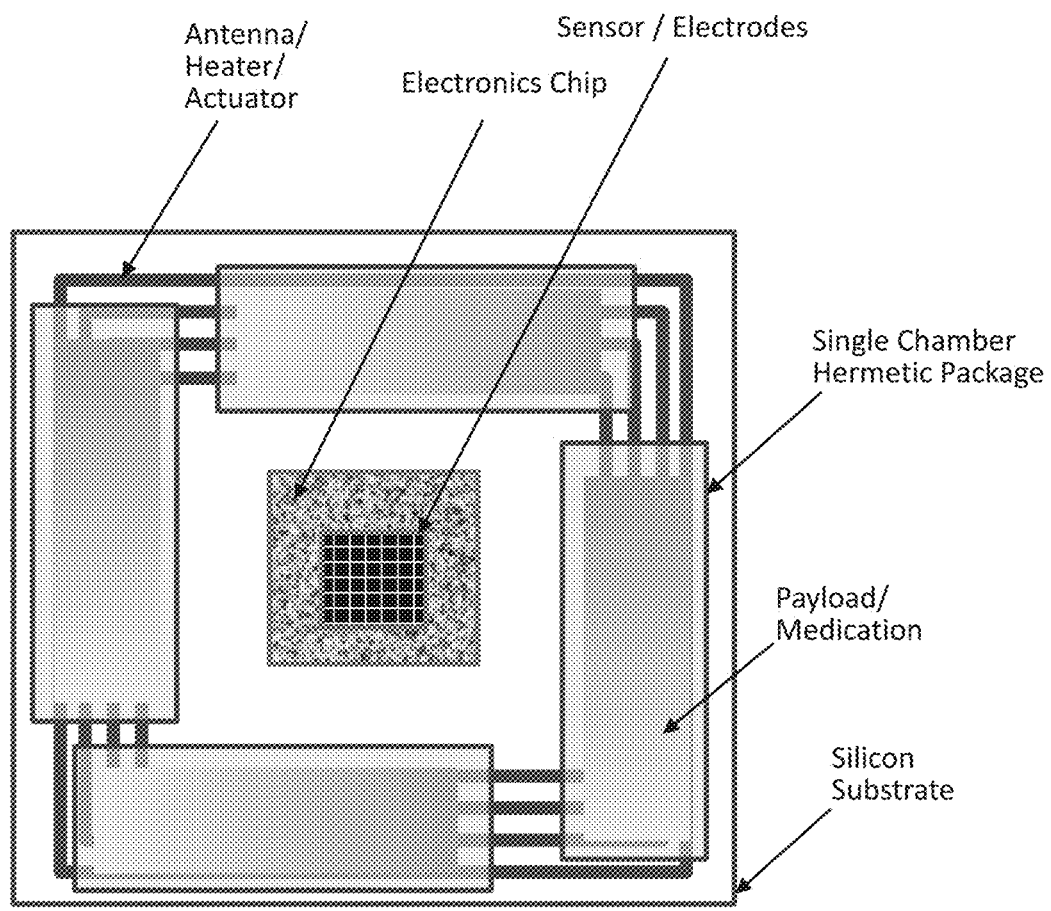
FIG. 31 shows a simplified top view of a wireless implantable drug delivery device according to an embodiment of the present disclosure comprising multiple chambers.

As discussed above, the wireless implantable drug delivery device according to the present disclosure can be fitted with sensors similar to sensors used in the above discussed wireless implantable sensing device with minimal impact on the size of the combined device as same electronic components can be used for both actuation of the sealed chamber and sensing (e.g. see circuits of FIGS. 13, 23 and 24). Electronic components of such system are depicted in FIG. 30 and described in the above description as related to FIGS. 13, 23 and 24. By virtue of being fitted with electrochemical sensing capability, the implantable device according to the present disclosure can perform the task of dispensing the medication based on sensed species. According to further embodiments of the present disclosure, an amount of the dispensed medication can be a function of a measured concentration of sensed species. By providing a plurality of chambers of known volumetric size containing a medication to be delivered, seal of one or more of such chambers can be ruptured by way of techniques (heat, pressure) described above based on the measured concentration. A corresponding top view of such implantable device is shown in FIG. 31, which shows four chambers mounted on areas comprising the coils of the antenna/heater/actuator element, and a sensor (with corresponding electrodes) mounted in the central area of the implantable device atop the electronics chip. A person skilled in the art would know of other possible layouts of the implantable device according to the present disclosure, and therefore the exemplary layouts shown in the various figures (e.g. 25, 27A, 27B, 28, 29 and 31) should not be considered as limiting the scope of the present invention. The person skilled in the art would use the various principles of operation, including actuation, interface, powering, sensing and dispensing as described above in implantable devices having different layouts than ones described above. In particular, size and positioning of the chamber containing the medication to be delivered may vary as best suited for a given application.

The wireless implantable devices described in the present disclosure can be used for continuous in-vivo monitoring of disease biomarkers and treatment efficacy and for telemetric delivery of therapeutic reagents with spatial and temporal control. Prior art efforts to continuously monitor analytes in-vivo follow a strategy of copying established in-vitro approaches such as binding chemistries, enzyme electrochemistry measurements, or hybridization sensing. However, such traditional approaches have known shortcomings, such as (a) limited lifetime of the devices as the surface functionalization coating deteriorates with time, (b) lack of specificity resulting from the extreme complexity of most body fluids compared to benchtop laboratory testing systems where filtration and pre-concentration of such body fluids is possible, and (c) the need to clean the surfaces periodically to avoid bio-fouling. Moreover, there are only a few chemistries that have been demonstrated for stable measurement of a limited set of analytes, such as glucose or lactate. As known to a person skilled in the art, glucose oxidase or dehydrogenase, for example, converts glucose to gluconic acid and releases a hydrogen peroxide ion in the process that can function in-vivo for approximately three weeks, mainly as a result of enzyme degradation. In particular, binding reactions can be problematic to monitor over long periods of time in-vivo, since the functionalized measurement surface must be periodically cleaned, requiring aptamers or other thermally stable chemistries to be deployed. In contrast, the commonly used antibody binding assays for in-vitro tests require only one-time binding and no cleaning. Many interesting chemistries, such as cytokines (as inflammation indicators) or micro-RNAs (ribonucleic acid) cannot be readily measured because of a lack of specific surface chemistry and their folded or sheathed geometries in exosomes.

In order to circumvent the above mentioned shortcomings with respect to the traditional approaches for in-vivo monitoring of chemistries, methods according to the present disclosure monitor changes in in-vivo chemistries with cell cultures or colonies that are selected to be very sensitive and specific to the analytes that need to be detected. Physiological characteristics and/or metabolic "wellness" of these cell cultures or colonies can be in turn monitored with, for example, the wireless implantable devices of the present disclosure, or any conventional electrochemical micro-sensors that can measure stable ion or analyte concentrations, or even light from fluorescence generated by red or green fluorescent proteins (GFP).

Methods according to the present disclosure for in-vivo monitoring of chemistries can allow measurement of the metabolic reaction of the cultured cells to the analytes of interest. One of the key advantages of this approach stems from the ability of such a biological interface between the cultured cells and the analytes to unfold and recognize (via integrated sensors) molecules that are typically folded, such as cytokines or even exosomes, tasks that are exceedingly difficult with current hardware and methods of use. For example, specifically selected cell colonies can sense genomic markers like micro-RNAs or circulating DNAs, exosomes and cytokine molecules in blood, interstitial fluid, urine or saliva. Moreover, it is not necessary to continuously clean surface contacts from bio-fouling products if the cell colonies and metabolic measurements are carefully selected.

In an exemplary case of the in-vivo monitoring methods according to the present disclosure, fluorescent protein markers are used and a corresponding optical signal can be recognized (e.g. via optical sensor in an implantable device) without the need of any open electrode surfaces, therefore rendering cleaning of surface coatings unnecessary. An implanted wireless device fitted with an optical sensor can detect fluorescence emitted by the fluorescent protein markers that reacted with an analyte. An exemplary case of such implantable wireless device is described, for example, in US Patent Publication No. 2014/0228660 entitled "Miniaturized Implantable Electrochemical Sensor Devices", published Aug. 14, 2014 which is herein incorporated by reference in its entirety.

In yet another exemplary case of the in-vivo monitoring methods according to the present disclosure, health ("wellness") of cells can be observed/monitored by measuring ions or body gases (pH, NO, CO, O2 etc.). Such in-vivo monitoring simply requires ion membranes and ionophores for selectivity, and does not require enzymes or surface coatings that could deteriorate with time.

As mentioned above, the in-vivo monitoring methods according to the present disclosure can use the minimally invasive wireless implantable devices of the present disclosure to take advantage of the built in electrochemical measurement capabilities as well as the built in drug delivery capabilities. The built in micro-sensors monitor the response of cells (that take the place of canaries in coal-mines) to the specific analytes. The in-vivo lifetimes of these wireless implantable devices is expected to outpace modern analyte detection for months to years without the risk of infection.

Figure 32:
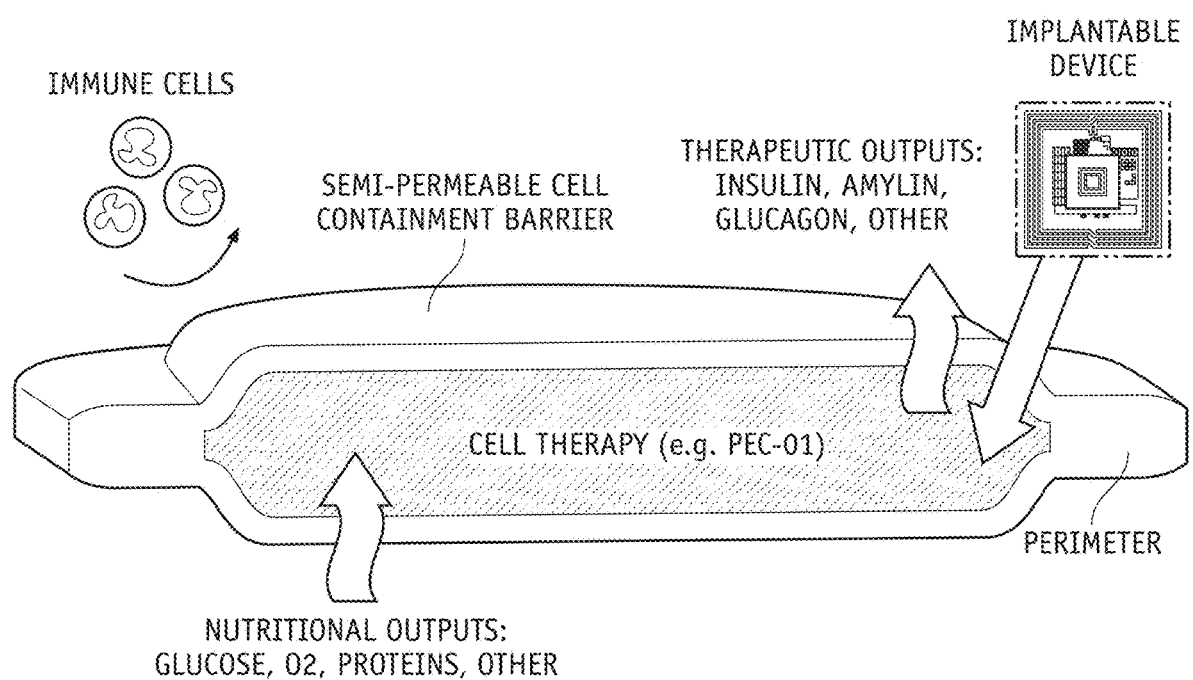
FIG. 32 shows a simplified rendering of an in-vivo bio-electronic system according to an embodiment of the present disclosure that is protected by a semi-permeable cell containment barrier.

According to a further embodiment of the present disclosure, an in-vivo bio-electronic system is presented which can monitor the health of cell colonies or cultures and accordingly dispense corresponding therapeutic drugs. Such in-vivo bio-electronic system comprises cellular interfaces formed by cells that are sensitive to specific chemistries, and a wireless implantable device of the present disclosure containing therapeutic sources (drugs) that can be used to produce in-vivo local therapy of the cells in response to sensed reactions, by the implantable device, of the cellular interface. According to further embodiments of the present disclosure, the in-vivo bio-electronic system is protected by a semi-permeable cell containment barrier, such as an organic pouch or parylene, as shown in FIG. 32.

According to one exemplary embodiment of the present disclosure, the cells of the in-vivo bio-electronic system are genetically engineered cells, designed, for example, for longevity and selectivity to specific molecules (e.g. cytokines, microRNAs, etc.). The in-vivo bio-electronic system according to the present disclosure, can therefore integrate CMOS sensor "intelligence" with genetically engineered cells that produce in-vivo local therapy on demand. Such closed-loop, in-vivo bio-electronic system of the present disclosure, can therefore resemble to an "artificial organ" in which disease measurement and therapeutic drug production are combined.

According to a further exemplary embodiment of the present disclosure, the in-vivo bio-electronic system according to the present disclosure comprises the wireless implantable device of the present disclosure fitted with sensors (functionalization layer) that can track physiological changes of indicator cell colonies in response to chemo- or immuno-therapy. Accordingly, the wireless implantable device can monitor and control indicator cell colonies by first detecting an inflammation, and then delivering a local therapy (dispensing drug). Such hybrid biological/electronic monitoring system can therefore resemble to an "artificial organ" remotely controlled through a conventional (e.g. CMOS) electronic interface.

The above methods and systems using the wireless implantable device of the present disclosure are transformative and can overcome some of the major impediments in preventive healthcare by developing minimally invasive implants to more efficiently monitor and treat many chronic and inflammatory disorders with long lifetimes.

Teachings according to the various embodiments of the present disclosure can be used for other applications related to implants by changing, for example, a corresponding system configuration. As noted in prior sections of the present disclosure (e.g. functionalization versatility), functionalization chemistry can be changed according to a desired sensing application, such as, for example, using urease instead of glucose oxidase to sense urea. The person skilled in the art can find numerous other examples while taking advantage of the present teachings.

A number of embodiments of the disclosure have been described. Nevertheless, it will be understood that various modifications may be made without departing from the spirit and scope of the present disclosure. Accordingly, other embodiments are within the scope of the following claims.

The examples set forth above are provided to those of ordinary skill in the art as a complete disclosure and description of how to make and use the embodiments of the disclosure, and are not intended to limit the scope of what the inventor/inventors regard as their disclosure.

Modifications of the above-described modes for carrying out the methods and systems herein disclosed that are obvious to persons of skill in the art are intended to be within the scope of the following claims. All patents and publications mentioned in the specification are indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a," "an," and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

LIST OF REFERENCES

[1]: G. Freckmann, S. Pleus, M. Link, E. Zschornack, H. Klotzer, C. Haug, "Performance Evaluation of Three Continuous Glucose Monitoring Systems: Comparison of Six Sensors Per Subject in Parallel," Journal of Diabetes Science and Technology, vol. 7, no. 4, pp. 842-853, July 2013.

[2]: M. M. Ahmadi, G. A. Julien, "A Wireless-Implantable Microsystem for Continuous Blood Glucose Monitoring," Transaction on Biomedical Circuits and Systems, vol. 3, no. 3, pp. 169-180, June 2009.

[3]: Y. T. Liao, H. Yao, A. Lingley, B. Parviz,B. Otis, "A 3 um CMOS Glucose Sensor for Wireless Contact-Lens Tear Glucose Monitoring," Journal of Solid-State Circuits, vol. 47, no. 1, pp. 335-344, January 2012.

[4]: S. O'Driscoll, A. Poon, T. Meng, "A mm-sized implantable power receiver with adaptive link compensation," International Solid-State Circuits Conference, pp. 294-295, February 2009.

[5]: Seese, "Characterization of tissue morphology, angiogenesis, and temperature in the adaptive response of muscle tissue in chronic heating, Lab. Invest. 1998; 78 (12): 1553-62.

[6]: Ward, "A Review of the Foreign-body Response to Subcutaneously-implanted Devices: The Role of Macrophages and Cytokines in Biofouling and Fibrosis", Journal of Diabetes Science and Technology, Vol. 2, Is. 5, September 2008.

The invention claimed is:

1. An integrated miniaturized implantable device comprising:
a substrate for monolithic integration comprising a plurality of metal layers separated via a plurality of insulating layers;
a monolithically integrated electronic system comprising an energy storage element adapted to be charged through a wireless communication link; and
a hermetic package comprising at least two separate chambers, including at least one chamber that contains a payload and at least one other chamber that contains an electrolyte that is spaced away from the payload, the hermetic package is in its entirety fixated on the first surface of the substrate with each of the at least two separate chambers adhered to the substrate,
wherein during operation of the implantable device, the electronic system is configured to:
communicate with an external device over the wireless communication link,
extract power for the miniaturized implantable device from the wireless communication link,
charge the energy storage element based on the extracted power, and
energize an actuator via the energy storage element rupturing a seal of the hermetic package.

2. The miniaturized implantable device according to claim 1, wherein the actuator is energized by current injected from the energy storage element to provide heat to the seal for rupturing of the seal.

3. The miniaturized implantable device according to claim 1, wherein the electrolyte contained in the hermetic package is in an electrolyte solution energized by current from the energy storage element to provide internal pressure for rupturing of the seal via gas released from an electrochemical dissociation reaction of the electrolyte solution.

4. The miniaturized implantable device according to claim 1, further comprising a monolithically integrated electrochemical sensor comprising a plurality of electrodes.

5. The miniaturized implantable device according to claim 1, wherein the energy storage element is a bank of capacitors charged through power extracted from the wireless communication link.

* * * * *